US007998464B2

(12) United States Patent
Lalleman

(10) Patent No.: US 7,998,464 B2
(45) Date of Patent: *Aug. 16, 2011

(54) PROCESS FOR THE PHOTOPROTECTIVE TREATMENT OF ARTIFICIALLY DYED KERATIN FIBERS BY APPLICATION OF A LIQUID WATER/STEAM MIXTURE

(75) Inventor: Boris Lalleman, Paris (FR)

(73) Assignee: L'Oreal S.A., Paris (FR)

( * ) Notice: Subject to any disclaimer, the term of this patent is extended or adjusted under 35 U.S.C. 154(b) by 797 days.

This patent is subject to a terminal disclaimer.

(21) Appl. No.: 11/528,454

(22) Filed: Sep. 28, 2006

(65) Prior Publication Data
US 2007/0074356 A1 Apr. 5, 2007

Related U.S. Application Data

(60) Provisional application No. 60/773,663, filed on Feb. 16, 2006.

(30) Foreign Application Priority Data

Sep. 29, 2005 (FR) .................... 05 52956

(51) Int. Cl.
A61K 8/00 (2006.01)
A61K 8/18 (2006.01)
(52) U.S. Cl. .......................... 424/70.1; 8/405
(58) Field of Classification Search ............. 8/405
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle et al. | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,463,264 A | 5/1949 | Graenacher et al. | |
| 2,961,347 A | 11/1960 | Floyd | |
| 3,206,462 A | 9/1965 | McCarty et al. | |
| 3,227,615 A | 1/1966 | Korden | |
| 3,874,870 A | 4/1975 | Green et al. | |
| 3,910,862 A | 10/1975 | Barabas et al. | |
| 3,912,808 A | 10/1975 | Sokol | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,075,136 A | 2/1978 | Schaper | |
| 4,137,180 A | 1/1979 | Naik et al. | |
| 4,165,367 A | 8/1979 | Chakrabarti | |
| 4,166,894 A | 9/1979 | Schaper | |
| 4,172,887 A | 10/1979 | Vanlerberghe et al. | |
| RE30,199 E | 1/1980 | Rose et al. | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,240,450 A | 12/1980 | Grollier et al. | |
| 4,277,581 A | 7/1981 | Vanlerberghe et al. | |
| 4,349,532 A | 9/1982 | Vanlerberghe et al. | |
| 4,381,919 A | 5/1983 | Jacquet et al. | |
| 4,422,853 A | 12/1983 | Jacquet et al. | |
| 4,445,521 A | 5/1984 | Grollier et al. | |
| 4,591,610 A | 5/1986 | Grollier | |
| 4,608,250 A | 8/1986 | Jacquet et al. | |
| 4,693,935 A | 9/1987 | Mazurek | |
| 4,719,099 A | 1/1988 | Grollier et al. | |
| 4,728,571 A | 3/1988 | Clemens et al. | |
| 4,761,273 A | 8/1988 | Grollier et al. | |
| 4,803,221 A | 2/1989 | Bair | |

(Continued)

FOREIGN PATENT DOCUMENTS

DE       23 59 399       6/1975

(Continued)

OTHER PUBLICATIONS

French Search Report for FR 0552956, dated Jul. 7, 2006.
Patrick D. Dorgan, "Waxes in Cosmetics," Drug and Cosmetic Industry, pp. 30-33 (1983).
William M. Meylan et al., "Atom-Fragment Contribution Method for Estimating Octanol-Water Partition Coefficients," Journal of Pharmaceutical Sciences, vol. 84, No. 1, pp. 83-92 (1995).
Charles Todd, "Volatile Silicone Fluids for Cosmetic Formulations," Cosmetics and Toiletries, vol. 91, pp. 29-32 (1976).
Anonymous, "The use of UV filters in cosmetic and pharmaceutical sunscreen formulations", IP Com Journal, 2002, pp. 1-35, New York, USA.
French Search Report corresponding to FR 05/51794, issued on Mar. 9, 2006, 4 pages.
European Search Report corresponding to EP 06 11 5282, issued on Oct. 19, 2006, 5 pages.

(Continued)

Primary Examiner — Tracy Vivlemore
Assistant Examiner — Jennifer Berrios
(74) Attorney, Agent, or Firm — Finnegan, Henderson, Farabow, Garrett & Dunner, LLP

(57) ABSTRACT

The present disclosure relates to a process for treating keratin fibers artificially dyed by direct dyeing or by oxidation dyeing, such as human hair, which comprises the application to the keratin fibers of a composition not containing any oxidation dye or any oxidizing agent and comprising at least one protective agent with a log P of less than or equal to 6, and then the application to the fibers of a liquid water/steam mixture at a temperature of at least 35° C. The present disclosure also relates to the use of the process for protecting keratin fibers artificially dyed by direct dyeing or by oxidation dyeing, such as human hair, against the action of atmospheric agents, such as against the action of light.

42 Claims, No Drawings

U.S. PATENT DOCUMENTS

| | | |
|---|---|---|
| 4,839,166 A | 6/1989 | Grollier et al. |
| 4,874,554 A | 10/1989 | Lange et al. |
| 4,948,579 A | 8/1990 | Jacquet et al. |
| 4,957,732 A | 9/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,061,289 A | 10/1991 | Clausen et al. |
| 5,089,252 A | 2/1992 | Grollier et al. |
| 5,139,037 A | 8/1992 | Grollier et al. |
| 5,196,189 A | 3/1993 | Jacquet et al. |
| 5,227,153 A | 7/1993 | Grollier et al. |
| 5,240,695 A | 8/1993 | Dubief et al. |
| 5,275,808 A | 1/1994 | Murray et al. |
| 5,362,485 A | 11/1994 | Hayama et al. |
| 5,380,340 A | 1/1995 | Neunhoeffer et al. |
| 5,451,395 A | 9/1995 | Murray et al. |
| 5,520,706 A | 5/1996 | Samain et al. |
| 5,534,267 A | 7/1996 | Neunhoeffer et al. |
| 5,577,519 A | 11/1996 | Samain et al. |
| 5,585,091 A | 12/1996 | Pelzer et al. |
| 5,616,746 A | 4/1997 | Mahieu et al. |
| 5,618,523 A | 4/1997 | Zysman et al. |
| 5,663,366 A | 9/1997 | Neunhoeffer et al. |
| 5,695,748 A | 12/1997 | Francis |
| 5,708,151 A | 1/1998 | Möckli |
| 5,766,576 A | 6/1998 | Löwe et al. |
| 5,773,611 A | 6/1998 | Zysman et al. |
| 5,792,221 A | 8/1998 | Lagrange et al. |
| 5,958,392 A | 9/1999 | Grollier et al. |
| 6,001,376 A | 12/1999 | Mahieu et al. |
| 6,076,530 A | 6/2000 | Braida-Valerio et al. |
| 6,093,385 A | 7/2000 | Habeck et al. |
| 6,099,592 A | 8/2000 | Vidal et al. |
| 6,099,593 A | 8/2000 | Terranova et al. |
| 6,159,455 A | 12/2000 | Habeck et al. |
| 6,191,301 B1 | 2/2001 | Habeck et al. |
| 6,210,691 B1 | 4/2001 | Mahieu et al. |
| 6,211,125 B1 | 4/2001 | Crudele et al. |
| 6,238,649 B1 | 5/2001 | Habeck et al. |
| 6,284,003 B1 | 9/2001 | Rose et al. |
| 6,338,741 B1 | 1/2002 | Vidal et al. |
| 6,387,355 B2 | 5/2002 | Heidenfelder et al. |
| 6,391,289 B2 | 5/2002 | Heidenfelder et al. |
| 6,436,373 B1 | 8/2002 | Habeck et al. |
| 6,545,174 B2 | 4/2003 | Habeck et al. |
| 6,645,258 B2 | 11/2003 | Vidal et al. |
| 6,740,317 B1 | 5/2004 | Cho et al. |
| 7,166,137 B2 * | 1/2007 | Narasimhan et al. ............ 8/405 |
| 2002/0001570 A1 | 1/2002 | Heidenfelder et al. |
| 2002/0004034 A1 | 1/2002 | Heidenfelder et al. |
| 2002/0016310 A1 | 2/2002 | Habeck et al. |
| 2002/0050013 A1 | 5/2002 | Vidal et al. |
| 2002/0139384 A1 | 10/2002 | Kamis et al. |
| 2003/0019051 A9 | 1/2003 | Vidal et al. |
| 2005/0013782 A1 | 1/2005 | Goppel et al. |
| 2005/0013786 A1 | 1/2005 | Sabbagh et al. |
| 2005/0160537 A1 * | 7/2005 | Watkins et al. .................. 8/405 |
| 2007/0056121 A1 * | 3/2007 | Genain et al. .................... 8/405 |

FOREIGN PATENT DOCUMENTS

| | | | |
|---|---|---|---|
| DE | 38 43 892 A1 | 6/1990 | |
| DE | 41 33 957 A1 | 4/1993 | |
| DE | 44 02 929 C1 | 6/1995 | |
| DE | 44 20 736 C1 | 8/1995 | |
| DE | 44 24 530 A1 | 1/1996 | |
| DE | 44 24 533 A1 | 1/1996 | |
| DE | 195 43 988 A1 | 5/1997 | |
| DE | 197 46 694 A1 | 2/1999 | |
| DE | 197 55 649 A1 | 6/1999 | |
| DE | 198 55 649 A1 | 6/2000 | |
| DE | 100 51 773 A1 | 4/2002 | |
| DE | 101 62 844 A1 | 7/2003 | |
| EP | 0 080 976 B1 | 6/1983 | |
| EP | 0 186 507 A2 | 7/1986 | |
| EP | 0 227 994 B1 | 7/1987 | |
| EP | 0 329 032 B1 | 8/1989 | |
| EP | 0337 354 B1 | 10/1989 | |
| EP | 0 412 704 B1 | 2/1991 | |
| EP | 0 414 707 A1 | 2/1991 | |
| EP | 0 437 006 A1 | 7/1991 | |
| EP | 0 486 135 B1 | 5/1992 | |
| EP | 0 582 152 B1 | 2/1994 | |
| EP | 0 646 572 B1 | 4/1995 | |
| EP | 0 659 396 B1 | 6/1995 | |
| EP | 0 659 400 A1 | 6/1995 | |
| EP | 0 662 314 A1 | 7/1995 | |
| EP | 0 669 323 B1 | 8/1995 | |
| EP | 0 699 430 A1 | 3/1996 | |
| EP | 0 714 954 B1 | 6/1996 | |
| EP | 0 770 375 B1 | 5/1997 | |
| EP | 0 832 642 B1 | 4/1998 | |
| EP | 0 967 200 B1 | 12/1999 | |
| EP | 0 981 318 A1 | 3/2000 | |
| EP | 1 008 586 B1 | 6/2000 | |
| EP | 1 027 883 A1 | 8/2000 | |
| EP | 1 118 319 A1 | 7/2001 | |
| EP | 1 133 980 A2 | 9/2001 | |
| EP | 1 133 981 A2 | 9/2001 | |
| EP | 1 300 137 A2 | 4/2003 | |
| EP | 1 468 667 A1 | 10/2004 | |
| EP | 1 568 350 A2 | 8/2005 | |
| FR | 1 011 151 | 6/1952 | |
| FR | 2 077 143 | 10/1971 | |
| FR | 2 080 759 | 11/1971 | |
| FR | 2 162 025 | 7/1973 | |
| FR | 2 190 406 | 2/1974 | |
| FR | 2 252 840 | 6/1975 | |
| FR | 2 270 846 | 12/1975 | |
| FR | 2 280 361 | 2/1976 | |
| FR | 2 316 271 | 1/1977 | |
| FR | 2 320 330 | 3/1977 | |
| FR | 2 336 434 | 7/1977 | |
| FR | 2 368 508 | 5/1978 | |
| FR | 3 383 660 | 10/1978 | |
| FR | 2 393 573 | 1/1979 | |
| FR | 2 413 907 | 8/1979 | |
| FR | 2 470 596 | 6/1981 | |
| FR | 2 505 348 | 11/1982 | |
| FR | 2 519 863 | 7/1983 | |
| FR | 2 542 997 | 9/1984 | |
| FR | 2 589 476 A1 | 5/1987 | |
| FR | 2 598 611 A1 | 11/1987 | |
| FR | 2 627 085 A1 | 8/1989 | |
| FR | 2 673 179 A1 | 8/1992 | |
| FR | 2 673 839 A1 | 9/1992 | |
| FR | 2 692 572 A1 | 12/1993 | |
| FR | 2 713 929 A1 | 6/1995 | |
| FR | 2 733 749 A1 | 11/1996 | |
| FR | 2 750 048 A1 | 12/1997 | |
| GB | 1 026 978 | 4/1966 | |
| GB | 1 153 196 | 5/1969 | |
| GB | 1 546 809 | 5/1979 | |
| JP | 2-19576 | 1/1990 | |
| JP | 5-43437 | 2/1993 | |
| JP | 5-163124 | 6/1993 | |
| JP | 7-187961 | 7/1995 | |
| JP | 2001-213741 A | 8/2001 | |
| WO | WO 93/11103 | 6/1993 | |
| WO | WO 93/23009 | 11/1993 | |
| WO | WO 93/23446 | 11/1993 | |
| WO | WO 94/07844 | 4/1994 | |
| WO | WO 94/08969 | 4/1994 | |
| WO | WO 94/08970 | 4/1994 | |
| WO | WO 94/10131 | 5/1994 | |
| WO | WO 94/24097 | 10/1994 | |
| WO | WO 95/00578 | 1/1995 | |
| WO | WO 95/01772 | 1/1995 | |

| WO | WO 95/15144 | 6/1995 |
| WO | WO 95/16665 | 6/1995 |
| WO | WO 95/23807 | 9/1995 |
| WO | WO 96/15765 | 5/1996 |
| WO | WO 98/51265 A1 | 11/1998 |
| WO | 99/37281 * | 7/1999 |
| WO | WO 2004/098550 A1 | 11/2004 |

OTHER PUBLICATIONS

Co-Pending U.S. Appl. No. 11/476,076; Title: Photoprotective Treatment of Keratin Fibers by Application of Heat; filed Jun. 28, 2006.
English language Derwent abstract for DE 100 51 773 A1, 2002.
English language Derwent abstract for JP 2001-213741 A, 2001.

* cited by examiner

PROCESS FOR THE PHOTOPROTECTIVE TREATMENT OF ARTIFICIALLY DYED KERATIN FIBERS BY APPLICATION OF A LIQUID WATER/STEAM MIXTURE

This application claims benefit of U.S. Provisional Application No. 60/773,663, filed Feb. 16, 2006, the contents of which are incorporated herein by reference. This application also claims benefit of priority under 35 U.S.C. §119 to French Patent Application No. FR 05 52956, filed Sep. 29, 2005, the contents of which are also incorporated herein by reference.

The present disclosure relates to a process for treating keratin fibers, such as human hair, artificially dyed by direct dyeing or by oxidation dyeing, which comprises the application to the keratin fibers of a composition not containing any oxidation dye or any oxidizing agent and comprising at least one protective agent with a log P of less than or equal to 6, followed by the application to the fibers of a liquid water/steam mixture at a temperature of at least 35° C.

The present disclosure also relates to the use of this process for protecting keratin fibers, such as human hair, artificially dyed by direct dyeing or by oxidation dyeing, against the action of atmospheric agents, for example, light.

It is well known that the hair is sensitized or embrittled to varying degrees by the action of atmospheric agents such as light. Many publications disclose that natural light destroys certain amino acids of the hair. These attacking factors may impair the hair fiber and reduce its mechanical properties, for instance the tensile strength, the breaking load and the elasticity, or its resistance to swelling in an aqueous medium. The hair then may be dull, coarse and brittle.

It is also known that light has a tendency to attack the natural color of the hair, and also the artificial color of dyed hair. The color of the hair may gradually fade or turn to relatively unattractive or undesirable shades.

The effect of light is even more visible on hair dyed by artificial coloration, such as oxidation dyeing or direct dyeing. In this case, exposure to light may lead to degradation of the dyes present both in the hair and on its surface. This typically results in substantial fading and/or changing of the color of the hair.

Substances for protecting the hair against the degradation caused by atmospheric attacking factors, such as light, have been sought for many years in the cosmetics industry. Products that protect the integrity of keratin fibers, i.e., their composition, their surface condition, their natural or artificial color and their intrinsic mechanical properties (the tensile strength, breaking load and elasticity, or their resistance to swelling in an aqueous medium) are sought in particular.

To combat these types of degradation of hair keratin, it has been proposed to use protecting agents such as organic UV-screening agents, antioxidants, chelating agents or free-radical scavengers.

Certain substances capable of screening out light radiation, for instance 2-hydroxy-4-methoxybenzophenone-5-sulfonic acid or salts thereof (French Patent Application No. FR-A-2 627 085), 4-(2-oxo-3-bornylidenemethyl)benzenesulfonic acid or salts thereof (European Patent Application No. EP-A-329 032) or lactoferrin (French Patent Application No. FR-A-2 673 839) have thus been proposed.

Japanese Patent Application No. JP 05-043437 discloses dye compositions containing 2-hydroxy-4-methoxybenzophenone-5-sulfonic acid or salts thereof, an aromatic alcohol and an acidic direct dye.

However, the current cosmetic compositions containing protective agents are not entirely satisfactory, such as on hair dyed with blue oxidation dyes, for instance those obtained with couplings comprising meta-phenylenediamines.

It has been proposed to treat, with a gas comprising steam, hair dyed by oxidation (application of a composition comprising at least one oxidation dye precursor and of a composition comprising at least one oxidizing agent) in order to accelerate the dyeing process, in French Patent No. FR-1 011 151, or to reduce the selectivity of the hair after dyeing, in European Patent No. EP 0 659 396.

It has been proposed in French Patent No. FR 2 713 929 to treat, with a gas comprising steam, hair that has undergone bleaching by applying a composition containing an oxidizing agent, in order to obtain rapid bleaching that does not generate any ginger tint.

The present inventors have now discovered, surprisingly, a novel process for treating keratin fibers, such as human hair, artificially dyed by direct dyeing or by oxidation dyeing, comprising the application to the keratin fibers of a composition not containing any oxidation dye or any oxidizing agent and comprising at least one protective agent with a log P of less than or equal to 6, followed by the application to the fibers of a liquid water/steam mixture at a temperature of at least 35° C.

This process may afford better protection of the fibers against the action of atmospheric agents and against the harmful effects of light.

An improvement in the light-fastness of the coloration of hair dyed by direct dyeing or by oxidation dyeing may be obtained by means of this process. The treatment process according to the present disclosure can also provide a light-protective effect that withstands shampooing.

All these discoveries form the basis of the present disclosure.

Thus, according to the present disclosure, a process is now disclosed for treating keratin fibers, such as human hair, artificially dyed by direct dyeing or by oxidation dyeing, comprising applying to the keratin fibers a composition not containing any oxidation dye or any oxidizing agent and comprising, in a physiologically acceptable medium, at least one protective agent with a log P of less than or equal to 6, followed by applying to the fibers a liquid water/steam mixture at a temperature of at least 35° C.

The term "not containing any oxidation dye" means not containing any oxidation dye precursor such as bases or couplers in an amount sufficient for oxidation dyeing the keratin fibers on contact with an oxidizing agent.

The term "not containing any oxidizing agent" means not containing any oxidizing agent in an amount for bleaching keratin fibers by oxidation.

Another aspect of the present disclosure relates to the use of the process for protecting keratin fibers against the action of atmospheric agents, for example, in one embodiment, against the action of light.

One aspect of the present disclosure relates to the use of the process as a post-treatment to oxidation dyeing or direct dyeing of keratin fibers, such as the hair.

Another aspect of the present disclosure relates to a process for dyeing keratin fibers, such as human hair, comprising:
a) direct dyeing or oxidation dyeing the fibers;
b) applying to the fibers a composition not containing any oxidation dye or any oxidizing agent and comprising, in a physiologically acceptable medium and a cosmetically acceptable medium, at least one protective agent with a log P of less than or equal to 6; and
c) applying to the fibers a liquid water/steam mixture at a temperature of at least 35° C.

The process according to the disclosure is applicable to any human keratin fiber in general, such as, for example, eyelashes, moustaches, body hairs and other hairs.

All of the meanings and definitions of the compounds used in the present disclosure given below apply to all of the subjects of the present disclosure.

In the context of the present disclosure, the log P value represents the partition coefficient of the dye between octanol and water. The log P value may be calculated according to the method described in the article by Meylan and Howard "Atom/Fragment contribution method for estimating octanol-water partition coefficient", J. Pharm. Sci. 84: 83-92, 1995. This value may also be calculated by means of numerous software packages available on the market, which determine the log P value as a function of the structure of a molecule. By way of example, the Epiwin software from the United States Environmental Agency and the Virtual Computational Chemistry Laboratory software may be mentioned.

The liquid water/steam mixture may constitute a mist. The mixture may also contain at least one other gas such as oxygen or nitrogen, mixtures of gases such as air, or other vaporizable compounds.

In at least one embodiment, the temperature of the liquid water/steam mixture is greater than or equal to 40° C., such as, for example, from 40° C. to 75° C.

In at least one embodiment, the liquid water/steam mixture is placed in contact with the fiber for a time ranging from 1 second to 1 hour, such as, for example, from 5 minutes to 15 minutes. The application of the mixture may be repeated several times on the same fiber, each operation being performed for a time as indicated above.

According to at least one embodiment of the process according to the present disclosure, the process comprises first applying to the hair a composition containing at least one photoprotective agent, and then subjecting these locks thus impregnated to the action of the liquid water/steam mixture under the conditions mentioned above, and then cooling the locks thus treated, for example by sending over or through them a stream of cold air or of air at ambient temperature.

The liquid water/steam mixture used according to the present disclosure may be produced using any apparatus known per se and intended for this purpose. According to at least one embodiment of the present disclosure, an apparatus comprising at least one steam generator directly connected to a hood that diffuses the liquid water/steam mixture onto the keratin fibers, such as human hair, is used. One example of an apparatus that can be used is that sold under the name Micromist® by the company Takara Belmont.

The at least one keratin fiber protective agent may be any active agent that is useful for preventing or limiting the degradation of keratin fibers, such as the hair, caused by atmospheric attacking factors, such as light.

In at least one embodiment, the at least one keratin fiber protective agent may be chosen from organic UV-screening agents, free-radical scavengers and antioxidants.

The term "free-radical scavenger" means any compound capable of trapping free radicals.

According to at least one embodiment, the organic UV-screening agents (systems for screening out UV radiation) are chosen from water-soluble or liposoluble screening agents.

In at least one embodiment, the organic screening agents are chosen from dibenzoylmethane derivatives; anthranilates; cinnamic derivatives; salicylic derivatives; camphor derivatives; benzophenone derivatives; β,β-diphenylacrylate derivatives; benzotriazole derivatives; triazine derivatives; benzalmalonate derivatives; benzimidazole derivatives; imidazolines; bis-benzazolyl derivatives as described in European Patent No. EP 669 323 and U.S. Pat. No. 2,463,264; p-aminobenzoic acid (PABA) derivatives; benzoxazole derivatives as described in European Patent Application Nos. EP 0 832 642, EP 1 027 883, and EP 1 300 137, and German Patent Application No. DE 101 62 844; dimers derived from α-alkylstyrene, such as those described in German Patent Application No. DE 198 55 649; 4,4-diarylbutadienes such as those described in European Patent Application Nos. EP 0 967 200, EP-A-1 008 586, EP 1 133 980 and EP 133 981, and German Patent Application Nos. DE 197 46 654 and DE 197 55 649, and mixtures thereof.

As examples of organic UV-screening agents, non-limiting mention may be made of those denoted hereinbelow under their INCI name:

Para-Aminobenzoic Acid Derivatives:
PABA,
Ethyl PABA,
Ethyl dihydroxypropyl PABA,
Ethylhexyl dimethyl PABA sold in particular under the name "Escalol 507" by ISP,
Glyceryl PABA,
PEG-25 PABA sold under the name "Uvinul P25" by BASF.

Cinnamic Derivatives:
Ethylhexyl methoxycinnamate sold in particular under the trade name "Parsol MCX" by Hoffmann LaRoche,
Isopropyl methoxycinnamate,
Isoamyl methoxycinnamate sold under the trade name "Neo Heliopan E 1000" by Haarmann and Reimer,
Cinoxate,
DEA methoxycinnamate,
Diisopropyl methylcinnamate.

Dibenzoylmethane Derivatives:
Butylmethoxydibenzoylmethane sold especially under the trade name "Parsol 1789" by Hoffmann LaRoche,
Isopropyldibenzoylmethane sold especially under the trade name "Eusolex 8020" by Merck.

Salicylic Derivatives:
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

β,β-Diphenylacrylate Derivatives:
Etocrylene sold, for example, under the trade name "Uvinul N35" by BASF.

Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF.

Benzylidenecamphor Derivatives:
3-Benzylidenecamphor manufactured under the name "Mexoryl SD" by Chimex,
4-Methylbenzylidenecamphor sold under the name "Eusolex 6300" by Merck, Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex.
Phenylbenzimidazole Derivatives:
Phenylbenzimidazolesulfonic acid sold in particular under the trade name "Eusolex 232" by Merck,
Disodium phenyldibenzimidazoletetrasulfonate sold under the trade name "Neo Heliopan AP" by Haarmann and Reimer.
Imidazoline Derivatives:
Ethylhexyldimethoxybenzylidenedioxoimidazoline propionate.

As liposoluble (or lipophilic) organic UV-screening agents that may be used according to the present disclosure, non-limiting mention may be made of:
Ethylhexyl methoxycinnamate,
Butylmethoxydibenzoylmethane,
Ethylhexyl salicylate,
Benzophenone-3,
4-Methylbenzylidenecamphor.

In at least one embodiment, the free-radical scavengers that may be used in the composition according to the present disclosure comprise vitamin E and derivatives thereof such as tocopheryl acetate; bioflavonoids; certain enzymes, for instance catalase, superoxide dismutase and wheatgerm extracts containing it, lactoperoxidase, glutathione peroxidase and quinone reductases; benzylcyclanones; substituted naphthalenones; pidolates; guanosine; lignans; and melatonin.

According to at least one embodiment, the antioxidants are chosen from phenols such as BHA (tert-butyl-4-hydroxyanisole), BHT (2,6-di-tert-butyl-p-cresol), TBHQ (tert-butylhydroquinone), polyphenols such as proanthocyanidol oligomers and flavonoids, hindered amines known under the generic term HALS (Hindered Amine Light Stabilizer) such as tetraaminopiperidine, erythorbic acid, polyamines such as spermine, superoxide dismutase or lactoferrin.

In at least one embodiment, the at least one keratin fiber protective agent is chosen from organic UV-screening agents.

According to at least one embodiment of the present disclosure, the at least one keratin fiber protective agent is present in an amount ranging from 0.15% to 50% by weight, such as, for example, from 0.35% to 30% by weight or from 0.5% to 20% by weight, relative to the total weight of the composition.

According to at least one embodiment of the present disclosure, the at least one protective agent is chosen from protective agents with a log P (octanol/water partition coefficient) of less than 4.5, such as, for example, less than 2.

According to at least one embodiment of the present disclosure, the at least one protective agent is soluble in the aqueous medium of the composition, including, for example, protective agents that are soluble at 25° C. and to at least 0.5% in water or $C_1$-$C_4$ lower alcohols, for instance ethanol.

According to at least one embodiment of the present disclosure, the at least one protective agent is chosen from protective agents that have in their chemical structure at least one acid function in free or partially or totally salified form, such as carboxylic acid or sulfonic acid. In at least one embodiment, the at least one protective agent is chosen from protective agents having in their chemical structure at least one sulfonic acid function in free or partially or totally salified form.

In at least one embodiment, water-soluble organic UV-screening agents will be used, chosen from:
PABA,
PEG-25 PABA,
Benzylidenecamphorsulfonic acid,
Camphorbenzalkonium methosulfate,
Terephthalylidenedicamphorsulfonic acid,
Phenylbenzimidazolesulfonic acid,
Disodium phenyldibenzimidazoletetrasulfonate,
Benzophenone-4,
Benzophenone-5,
Benzophenone-9,
or mixtures thereof.

In at least one embodiment, benzophenone-4 is used.

The physiologically acceptable and cosmetically acceptable medium may comprise water or a mixture of water and at least one cosmetically acceptable organic solvent. Non-limiting examples of organic solvents that may be mentioned include $C_1$-$C_4$ lower alkanols such as ethanol and isopropanol; polyols and polyol ethers, for instance 2-butoxyethanol, propylene glycol, propylene glycol monomethyl ether and diethylene glycol monomethyl ether and monoethyl ether, and mixtures thereof.

In at least one embodiment, the solvents are present in an amount ranging from 1% to 40% by weight, such as, for example, from 3% to 30% by weight, approximately relative to the total weight of the dye composition.

The composition according to the present disclosure containing the at least one protective agent may also contain at least one adjuvant conventionally used in hair treatment compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, such as anionic, cationic, nonionic and amphoteric polymeric associative thickeners, penetrants, sequestrants, fragrances, buffers, dispersants, conditioning agents, for instance volatile or nonvolatile, modified or unmodified silicones, film-forming agents, ceramides, preserving agents and opacifiers.

According to at least one embodiment of the present disclosure, the hair compositions containing the at least one protective agent also comprise at least one aromatic alcohol and at least one aromatic carboxylic acid.

The term "aromatic alcohol" means any compound that is liquid at room temperature and atmospheric pressure, comprising at least one benzene or naphthalene ring and at least one alcohol function (OH) directly linked to the ring or linked to at least one substituent of the ring. In at least one embodiment, the alcohol function is a substituent of the benzene or naphthalene ring.

Among the aromatic alcohols that may be used in the composition according to the present disclosure, non-limiting mention may be made of:
benzyl alcohol
benzoylisopropanol
benzyl glycol
phenoxyethanol
dichlorobenzyl alcohol
methylphenylbutanol
phenoxyisopropanol
phenylisohexanol
phenylpropanol
phenylethyl alcohol
mixtures thereof.

In at least one embodiment, benzyl alcohol is used.

According to at least one embodiment of the present disclosure, the at least one aromatic alcohol may be present in an amount ranging from 0.01% to 50% by weight, such as, for example, from 0.1% to 30% by weight or from 1% to 20% by weight, relative to the total weight of the composition. In at least one embodiment, the at least one aromatic alcohol may be present in an amount greater than 1% by weight.

According to at least one embodiment, the hair compositions according to the present disclosure also comprise at least one optionally salified aromatic carboxylic acid.

The term "aromatic carboxylic acid" means any compound comprising at least one benzene or naphthalene ring and at least one carboxylic acid function (COOH), in free or salified form, directly linked to the ring or linked to at least one substituent of the ring. In at least one embodiment, the acid function is directly linked to the benzene or naphthalene ring.

The aromatic carboxylic acid salts may be chosen from alkali metal (sodium or potassium) or alkaline-earth metal (calcium or magnesium) salts or organic amine or ammonium salts.

Among the aromatic carboxylic acids that may be used in the composition according to the present disclosure, non-limiting mention may be made of:

benzoic acid
para-anisic acid
diphenolic acid
ferulic acid
hippuric acid
3-hydroxybenzoic acid
4-hydroxybenzoic acid
phenylthioglycolic acid
acetylsalicylic acid
para-, meta- or ortho-phthalic acid, and also the salified forms thereof, and mixtures thereof.

In at least one embodiment, benzoic acid is used.

According to at least one embodiment of the present disclosure, the at least one aromatic acid or salts thereof may be present in an amount ranging from 0.001% to 30% by weight, such as, for example, from 0.01% to 20% by weight or from 0.1% to 10% by weight, relative to the total weight of the composition.

The compositions according to the present disclosure may also contain at least one conditioning agent.

In the context of the present disclosure, the term "conditioning agent" means any agent whose function is to improve the cosmetic properties of the hair, such as softness, disentangling, feel, smoothness and static electricity.

The at least one conditioning agent may be in liquid, semi-solid or solid form such as, for example, oils, waxes or gums.

According to at least one embodiment of the present disclosure, the at least one conditioning agent may be chosen from synthetic oils such as polyolefins, plant or animal oils, fluoro oils or perfluoro oils, natural or synthetic waxes, silicones, non-polysaccharide cationic polymers, compounds of ceramide type, cationic surfactants, fatty amines, fatty acids and derivatives thereof, and also mixtures of these various compounds.

According to at least one embodiment, the synthetic oils are polyolefins, such as poly-α-olefins, for example:
of hydrogenated or non-hydrogenated polybutene type, such as hydrogenated or non-hydrogenated polyisobutene type.

Isobutylene oligomers with a molecular weight of less than 1000 and mixtures thereof with polyisobutylenes with a molecular weight of greater than 1000, such as from 1000 to 15,000, are used according to at least one embodiment.

As examples of poly-α-olefins that can be used in the context of the present disclosure, non-limiting mention may be made of the polyisobutenes sold under the name PERM-ETHYL 99 A, 101 A, 102 A, 104 A (n=16) and 106 A (n=38) by the company Presperse Inc., or alternatively the products sold under the name ARLAMOL HD (n=3) by the company ICI (n denoting the degree of polymerization),
of hydrogenated or non-hydrogenated polydecene type.

Such products are sold, for example, under the names ETHYLFLO by the company Ethyl Corp. and ARLAMOL PAO by the company ICI.

In at least one embodiment, the animal or plant oils are chosen from sunflower oil, corn oil, soybean oil, avocado oil, jojoba oil, marrow oil, grapeseed oil, sesame oil, hazelnut oil, fish oils, glyceryl tricaprocaprylate, or plant or animal oils of formula $R_9COOR_{10}$ wherein $R_9$ is a higher fatty acid residue containing from 7 to 29 carbon atoms and $R_{10}$ is chosen from linear and branched hydrocarbon-based chains containing from 3 to 30 carbon atoms, such as alkyl or alkenyl, for example purcellin oil or liquid jojoba wax.

It is also possible to use natural or synthetic essential oils such as, for example, eucalyptus oil, lavendin oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil.

In at least one embodiment, the at least one wax is a natural (animal or plant) or synthetic substance that is solid at room temperature (20°-25° C.). The at least one wax is insoluble in water, soluble in oils and are capable of forming a water-repellent film.

For the definition of waxes, mention may be made, for example, of P. D. Dorgan, Drug and Cosmetic Industry, December 1983, pp. 30-33.

According to at least one embodiment, the at least one wax is chosen from carnauba wax, candelilla wax, alfalfa wax, paraffin wax, ozokerite, plant waxes such as olive tree wax, rice wax, hydrogenated jojoba wax or the absolute waxes of flowers such as the essential wax of blackcurrant flower sold by the company Bertin (France), animal waxes such as beeswaxes, or modified beeswaxes (cerabellina); other waxes or waxy starting materials which can be used according to the disclosure are, for example, marine waxes such as the product sold by the company Sophim under the reference M82, and polyethylene waxes or polyolefin waxes in general.

The conditioning agents that are used according to at least one embodiment of the present disclosure are cationic polymers and silicones.

Non-saccharide cationic polymers that may be used in accordance with the present disclosure may be chosen from those already known per se as improving the cosmetic properties of hair treated with detergent compositions, such as those described in European Patent Application No. EP-A-0 337 354 and in French Patent Application Nos. FR-A-2 270 846, 2 383 660, 2 598 611, 2 470 596 and 2 519 863.

The term "non-saccharide polymers" is understood to mean polymers that do not contain a glycoside bond between monosaccharides.

For the purpose of the present disclosure, the term "cationic polymer" denotes any polymer containing cationic groups and/or groups that may be ionized into cationic groups.

Cationic polymers that are used according to at least one embodiment are chosen from those containing units comprising primary, secondary, tertiary and/or quaternary amine groups that either may form part of the main polymer chain or may be borne by a side substituent directly attached thereto.

In at least one embodiment, the cationic polymers used have a number-average molecular mass ranging from 500 to $5\times10^6$, such as, for example, from $10^3$ to $3\times10^6$.

Among the cationic polymers that may be used according to at least one embodiment of the present disclosure, non-limiting mention may be made of polymers of the polyamine, polyamino amide and polyquaternary ammonium type. These are known products.

Polymers of the polyamine, polyamino amide and polyquaternary ammonium type that may be used in accordance with at least one embodiment of the present disclosure, include those described in French Patent Nos. 2 505 348 and 2 542 997. Among these polymers, non-limiting mention may be made of:

(1) homopolymers or copolymers derived from acrylic or methacrylic esters or amides and comprising at least one of the units of the following formulae:

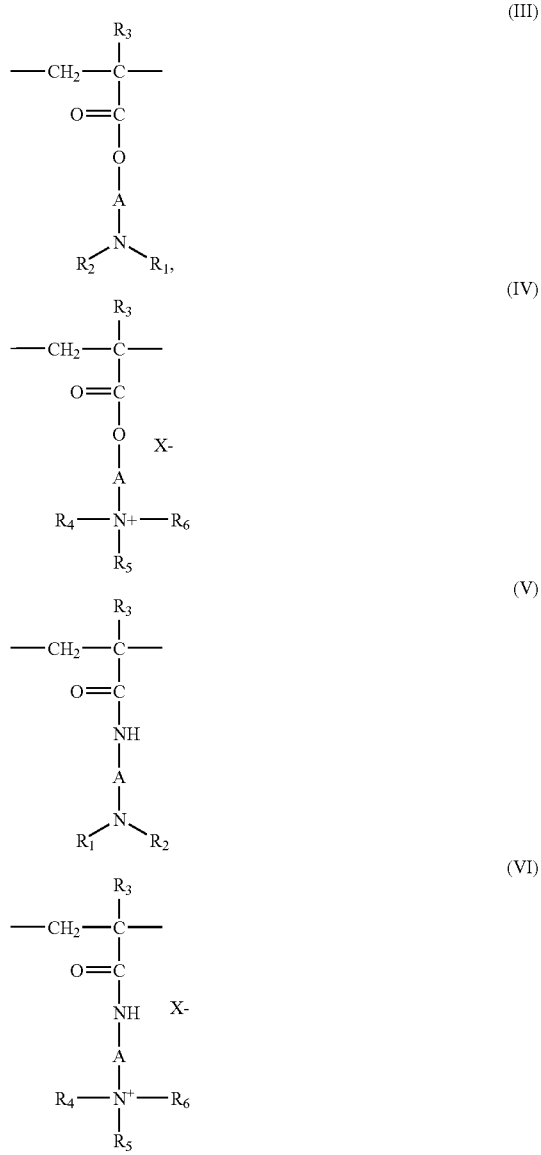

wherein:

$R_1$ and $R_2$, which may be identical or different, are chosen from hydrogen and alkyl groups containing from 1 to 6 carbon atoms, such as methyl or ethyl;

$R_3$, which may be identical or different, is chosen from hydrogen atoms and $CH_3$ radicals;

A, which may be identical or different, is chosen from linear and branched alkyl groups of 1 to 6 carbon atoms, such as, for example, 2 or 3 carbon atoms, and hydroxyalkyl groups of 1 to 4 carbon atoms;

$R_4$, $R_5$ and $R_6$, which may be identical or different, are chosen from alkyl groups containing from 1 to 18 carbon atoms, such as, for example, 1 to 6 carbon atoms, and benzyl radicals;

X is chosen from anions derived from a mineral or organic acid, such as a methosulfate anion or a halide such as chloride or bromide.

The copolymers of family (1) can also contain at least one unit derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), non-limiting mention may be made of:

copolymers of acrylamide and of dimethylaminoethyl methacrylate quaternized with dimethyl sulfate or with a dimethyl halide, such as the product sold under the name HERCOFLOC by the company Hercules, the copolymers of acrylamide and of methacryloyloxyethyltrimethylammonium chloride described, for example, in European Patent Application No. EP-A-080 976 and sold under the name BINA QUAT P 100 by the company Ciba Geigy, the copolymer of acrylamide and of methacryloyloxyethyltrimethylammonium methosulfate sold under the name RETEN by the company Hercules, quaternized or non-quaternized vinylpyrrolidone/dialkylaminoalkyl acrylate or methacrylate copolymers, such as the products sold under the name Gafquat by the company ISP, such as, for example, GAFQUAT 734 or GAFQUAT 755, or alternatively the products known as COPOLYMER 845, 958 and 937. These polymers are described in detail in French Patent Nos. 2 077 143 and 2 393 573, dimethylaminoethyl methacrylate/vinylcaprolactam/vinylpyrrolidone terpolymers, such as the product sold under the name GAFFIX VC 713 by the company ISP, vinylpyrrolidone/methacrylamidopropyldimethylamine copolymers sold, for example, under the name STYLEZE CC 10 by ISP, and quaternized vinylpyrrolidone/dimethylaminopropylmethacrylamide copolymers, such as the product sold under the name GAFQUAT HS 100 by the company ISP.

(2) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, as well as the oxidation and/or quaternization products of these polymers. Such polymers are described, for example, in French Patent Nos. 2 162 025 and 2 280 361.

(3) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, for example, in French Patent Nos. 2 252 840 and 2 368 508.

(4) The polyamino amide derivatives resulting from the condensation of polyalkylene polyamines with polycarboxylic acids followed by alkylation with difunctional agents. Non-limiting mention may be made, for example, of adipic acid/dialkylaminohydroxyalkyldialkylenetriamine polymers in which the alkyl radical contains from 1 to 4 carbon atoms, such as methyl, ethyl or propyl. Such polymers are described, for example, in French Patent No. 1 583 363.

Among these derivatives, non-limiting mention may be made of the adipic acid/dimethylaminohydroxypropyl/diethylenetriamine polymers sold under the name CARTARETINE F, F4 or F8 by the company Sandoz.

(5) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom being reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold, for example, under the name HERCOSETT 57 by the company Hercules Inc. or alternatively under the name PD 170 or DELSETTE 101 by the company Hercules in the case of the adipic acid/epoxypropyl/diethylenetriamine copolymer.

(6) Cyclopolymers of alkyldiallylamine or of dialkyldiallylammonium, such as the homopolymers or copolymers containing, as main constituent of the chain, units corresponding to formula (VII) or (VIII):

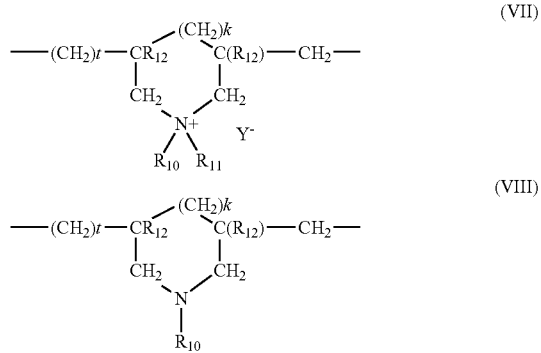

wherein:
k and t are equal to 0 or 1, the sum k+t being equal to 1;
$R_{12}$ is chosen from hydrogen atoms and methyl radicals;
$R_{10}$ and $R_{11}$, independently of each other, are chosen from alkyl groups having from 1 to 6 carbon atoms, hydroxyalkyl groups in which the alkyl group has, for example, from 1 to 5 carbon atoms, lower ($C_1$-$C_4$) amidoalkyl groups, or
$R_{10}$ and $R_{11}$, can denote, together with the nitrogen atom to which they are attached, heterocyclic groups such as piperidyl or morpholinyl;

$Y^-$ is chosen from anions such as bromide, chloride, acetate, borate, citrate, tartrate, bisulfate, bisulfite, sulfate or phosphate.

These polymers are described, for example, in French Patent No. 2 080 759 and in its Certificate of Addition 2 190 406.

In at least one embodiment, $R_{10}$ and $R_{11}$, independently of each other, are chosen from alkyl groups containing from 1 to 4 carbon atoms.

Among the polymers defined above, non-limiting mention may be made of the dimethyldiallylammonium chloride homopolymer sold under the name MERQUAT 100 by the company Nalco (and its homologues of low weight-average molecular mass) and the copolymers of diallyldimethylammonium chloride and of acrylamide, sold under the name MERQUAT 550.

(7) The quaternary diammonium polymer containing repeating units corresponding to the formula:

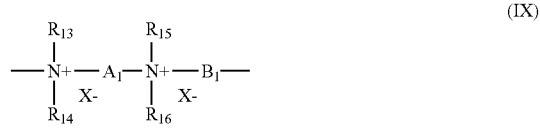

wherein in formula (IX):
$R_{13}$, $R_{14}$, $R_{15}$ and $R_{16}$, which may be identical or different, are chosen from aliphatic, alicyclic and arylaliphatic radicals containing from 1 to 20 carbon atoms and lower hydroxyalkylaliphatic radicals, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ are chosen from linear and branched $C_1$-$C_6$ alkyl radicals substituted with a nitrile, ester, acyl or amide group, or a group —CO—O—$R_{17}$-D or —CO—NH—$R_{17}$-D where $R_{17}$ is an alkylene and D is a quaternary ammonium group;

$A_1$ and $B_1$ are chosen from polymethylene groups containing from 2 to 20 carbon atoms which may be linear or branched, saturated or unsaturated, and which may contain, linked to or intercalated in the main chain, at least one aromatic ring or at least one oxygen or sulfur atom or sulfoxide, sulfone, disulfide, amino, alkylamino, hydroxyl, quaternary ammonium, ureido, amide or ester group, and $X^-$ is chosen from anions derived from a mineral or organic acid;

$A_1$, $R_{13}$ and $R_{15}$ can form, with the two nitrogen atoms to which they are attached, a piperazine ring; in addition, if $A_1$ is chosen from linear and branched, saturated and unsaturated alkylene and hydroxyalkylene radicals, $B_1$ can also be chosen from $(CH_2)_n$—CO-D-OC—$(CH_2)_n$—, n being an integer ranging from 2 to 20, wherein D is chosen from:
a) glycol residues of formula: —O—Z—O—, where Z is chosen from linear and branched hydrocarbon-based radicals and groups corresponding to one of the following formulae:

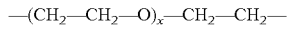

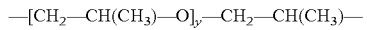

where x and y are chosen from integers from 1 to 4, representing a defined and unique degree of polymerization, and any number from 1 to 4 representing an average degree of polymerization;

b) bis-secondary diamine residues such as a piperazine derivative;

c) bis-primary diamine residues of formula: —NH—Y—NH—, where Y is chosen from linear and branched hydrocarbon-based radicals, and alternatively the divalent radical

—CH$_2$—CH$_2$—S—S—CH$_2$—CH$_2$—;

d) ureylene groups of formula: —NH—CO—NH—.

In at least one embodiment, X$^-$ is an anion such as chloride or bromide.

According to at least one embodiment, these polymers have a number-average molecular mass ranging from 1000 to 100,000.

Polymers of this type are described, for example, in French Patent Nos. 2 320 330, 2 270 846, 2 316 271, 2 336 434, and 2 413 907 and U.S. Pat. Nos. 2,273,780; 2,375,853; 2,388,614; 2,454,547; 3,206,462; 2,261,002; 2,271,378; 3,874,870; 4,001,432; 3,929,990; 3,966,904; 4,005,193; 4,025,617; 4,025,627; 4,025,653; 4,026,945; and 4,027,020.

In at least one embodiment, polymers are used that comprise repeating units corresponding to the formula:

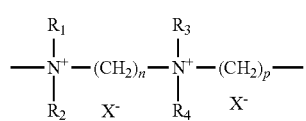

wherein:
R$_1$, R$_2$, R$_3$ and R$_4$, which may be identical or different, are chosen from alkyl and hydroxyalkyl radical containing from 1 to 4 carbon atoms,
n and p are integers ranging from 2 to 20, and
X$^-$ is chosen from anions derived from mineral or organic acids.

A compound of formula (a) that is used according to at least one embodiment is the compound for which R$_1$, R$_2$, R$_3$ and R$_4$ are methyl radicals and n=3, p=6 and X=Cl, referred to as hexadimethrine chloride according to the INCI nomenclature (CTFA).

(8) Polyquaternary ammonium polymers comprising units of formula (X):

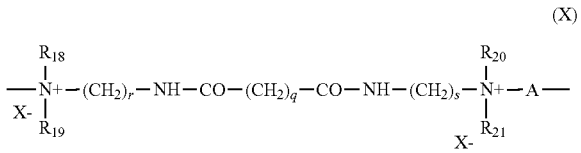

wherein:
R$_{18}$, R$_{19}$, R$_{20}$ and R$_{21}$, which may be identical or different, are chosen from hydrogen atoms and methyl, ethyl, propyl, β-hydroxyethyl, β-hydroxypropyl and —CH$_2$CH$_2$(OCH$_2$CH$_2$)$_p$OH radicals,
where p is equal to 0 or to an integer ranging from 1 to 6, with the proviso that R$_{18}$, R$_{19}$, R$_{20}$ and R$_{21}$ do not simultaneously represent a hydrogen atom, r and s, which may be identical or different, are integers ranging from 1 to 6,
q is equal to 0 or to an integer ranging from 1 to 34,
X$^-$ is chosen from anions such as a halide,
A is chosen from divalent radicals and —CH$_2$—CH$_2$—O—CH$_2$—CH$_2$—.

Such compounds are described, for example, in European Patent Application No. EP-A-122 324.

Among these products, non-limiting mention may be made, for example, of Mirapol® A 15, Mirapol® AD1, Mirapol® AZ1 and Mirapol® 175 sold by the company Miranol.

(9) Quaternary polymers of vinylpyrrolidone and of vinylimidazole, such as, for example, the products sold under the names Luviquat® FC 905, FC 550 and FC 370 by the company BASF.

(10) Crosslinked methacryloyloxy(C$_1$-C$_4$)alkyltri(C$_1$-C$_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, such as methylenebisacrylamide. A crosslinked acrylamide/methacryloyloxyethyltrimethylammonium chloride copolymer (20/80 by weight) in the form of a dispersion containing 50% by weight of the copolymer in mineral oil can be used in at least one embodiment. This dispersion is sold under the name Salcare® SC 92 by the company Ciba. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Ciba.

Other cationic polymers that can be used in at least one embodiment of the present disclosure are cationic proteins or cationic protein hydrolysates, polyalkyleneimines, such as polyethyleneimines, polymers containing vinylpyridine or vinylpyridinium units, condensates of polyamines and of epichlorohydrin, quaternary polyureylenes and chitin derivatives.

Among the cationic polymers that may be used in at least one embodiment of the present disclosure, cationic cyclopolymers can be used, such as the dimethyldiallyl-ammonium chloride homopolymers or copolymers sold under the names MERQUAT 100, MERQUAT 550 and MERQUAT S by the company Nalco, and quaternary vinylpyrrolidone and vinylimidazole polymers, and mixtures thereof.

Silicones that may be used in accordance with at least one embodiment of the present disclosure include polyorganosiloxanes that are insoluble in the composition and that may be in the form of oils, waxes, resins or gums.

The organopolysiloxanes are defined in greater detail in Walter Noll's "Chemistry and Technology of Silicones" (1968) Academic Press. They can be volatile or non-volatile.

When they are volatile, the silicones can be chosen from those having a boiling point ranging from 60° C. to 260° C., and in at least one embodiment are chosen from:

(i) cyclic silicones containing from 3 to 7, such as 4 to 5 silicon atoms. These are, for example, octamethylcyclotetrasiloxane sold, for example, under the name VOLATILE SILICONE 7207 by Union Carbide or SILBIONE 70045 V 2 by Rhodia Chimie, decamethylcyclopentasiloxane sold under the name VOLATILE SILICONE 7158 by Union Carbide, and SILBIONE 70045 V 5 by Rhodia Chimie, and mixtures thereof.

Non-limiting mention may also be made of cyclocopolymers of the dimethylsiloxanes/methylalkylsiloxane type, such as VOLATILE SILICONE FZ 3109 sold by the company Union Carbide, having the chemical structure:

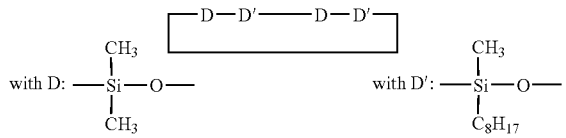

with D: $-\!\!\operatorname*{Si}(CH_3)(CH_3)\!-\!\!O\!-$  with D': $-\!\!\operatorname*{Si}(CH_3)(C_8H_{17})\!-\!\!O\!-$ Non-limiting mention may also be made of mixtures of cyclic silicones with organosilicone compounds, such as the mixture of octamethylcyclotetrasiloxane and tetra-trimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ m$^2$/s at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Non-volatile silicones, such as polyalkylsiloxanes, polyarylsiloxanes, polyalkylarylsiloxanes, silicone gums and resins, polyorganosiloxanes modified with organofunctional groups, and mixtures thereof, are used in at least one embodiment.

These silicones can be chosen from polyalkylsiloxanes, among which non-limiting mention may be made of polydimethylsiloxanes containing trimethylsilyl end groups having a viscosity of from $5 \times 10^{-6}$ to 2.5 m$^2$/s at 25° C., such as, for example, from $1 \times 10^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:

the SILBIONE oils of the 47 and 70 047 series or the MIRASIL oils sold by Rhodia Chimie, such as, for example, the oil 70 047 V 500 000;

the oils of the MIRASIL series sold by the company Rhodia Chimie;

the oils of the 200 series from the company Dow Corning, such as, for example, DC200 with a viscosity of 60,000 cSt;

the VISCASIL oils from General Electric and certain oils of the SF series (SF 96, SF 18) from General Electric.

Non-limiting mention may also be made of polydimethylsiloxanes containing dimethylsilanol end groups (Dimethiconol according to the CTFA name) such as the oils of the 48 series from the company Rhodia Chimie.

In this category of polyalkylsiloxanes, non-limiting mention may also be made of the products sold under the names ABIL WAX 9800 and 9801 by the company Goldschmidt, which are poly($C_1$-$C_{20}$)alkylsiloxanes.

According to at least one embodiment, the polyalkylarylsiloxanes are chosen from linear and branched polydimethylmethylphenylsiloxanes and polydimethyldiphenylsiloxanes with a viscosity of from $1 \times 10^{-5}$ to $5 \times 10^{-2}$ m$^2$/s at 25° C.

Among these polyalkylarylsiloxanes, non-limiting mention may be made, by way of example, of the products sold under the following names:
the SILBIONE oils of the 70 641 series from Rhodia Chimie;
the oils of the RHODORSIL 70 633 and 763 series from Rhodia Chimie;
the oil Dow Corning 556 Cosmetic Grade Fluid from Dow Corning;
the silicones of the PK series from Bayer, such as the product PK20;
the silicones of the PN and PH series from Bayer, such as the products PN1000 and PH1000; and
certain oils of the SF series from General Electric, such as SF 1023, SF 1154, SF 1250 and SF 1265.

The silicone gums that can be used in accordance with at least one embodiment of the present disclosure are, for example, polydiorganosiloxanes with high number-average molecular masses ranging from 200,000 to 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Non-limiting mention may also be made of the following products:
polydimethylsiloxane,
polydimethylsiloxane/methylvinylsiloxane gums,
polydimethylsiloxane/diphenylsiloxane,
polydimethylsiloxane/phenylmethylsiloxane, and
polydimethylsiloxane/diphenylsiloxane/methylvinylsiloxane.

Products that can be used in accordance with at least one embodiment of the present disclosure are mixtures such as:
mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;
mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane;
mixtures of two PDMSs with different viscosities, such as a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may contain 15% SE 30 gum and 85% SF 96 oil.

The organopolysiloxane resins that can be used in accordance with at least one embodiment of the present disclosure are crosslinked siloxane systems containing the following units:
$R_2SiO_{2/2}$, $R_3SiO_{1/2}$, $RSiO_{3/2}$ and $SiO_{4/2}$ wherein R is chosen from hydrocarbon-based groups containing 1 to 16 carbon atoms and a phenyl group. Among these products, at least one embodiment of the present disclosure comprises the ones in which R is chosen from $C_1$-$C_4$ lower alkyl radicals, such as methyl, and a phenyl radical.

Among these resins, non-limiting mention may be made of the product sold under the name Dow Corning 593 or those sold under the names SILICONE FLUID SS 4230 and SS 4267 by the company General Electric, which are silicones of dimethyl/trimethyl siloxane structure.

Non-limiting mention may also be made of the trimethylsiloxysilicate-type resins sold, for example, under the names X22-4914, X21-5034 and X21-5037 by the company Shin-Etsu.

The organomodified silicones that can be used in accordance with at least one embodiment of the present disclosure are silicones as defined above and comprising in their structure at least one organofunctional group attached via a hydrocarbon-based radical.

Among the organomodified silicones, non-limiting mention may be made of polyorganosiloxanes comprising:
  polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET L 722, L 7500, L 77 and L 711 by the company Union Carbide, and the ($C_{12}$)alkylmethicone copolyol sold by the company Dow Corning under the name Q2 5200;
  substituted or unsubstituted amine groups, such as the products sold under the name GP 4 SILICONE FLUID and GP 7100 by the company Genesee, or the products sold under the names Q2 8220 and Dow Corning 929 or 939 by the company Dow Corning. The substituted amine groups are, for example, $C_1$-$C_4$ aminoalkyl groups;
  thiol groups such as the products sold under the names GP 72 A and GP 71 from Genesee;
  alkoxylated groups such as the product sold under the name SILICONE COPOLYMER F-755 by SWS Silicones and ABIL WAX 2428, 2434 and 2440 by the company Goldschmidt;
  hydroxylated groups such as the polyorganosiloxanes containing a hydroxyalkyl function, described in French Patent Application No. FR-A-85/16334, corresponding to formula (XI):

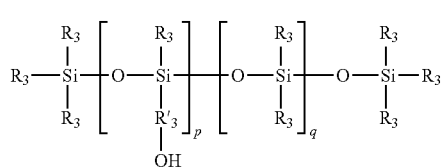
(XI)

wherein the radicals $R_3$, which may be identical or different, are chosen from methyl and phenyl radicals; at least 60 mol % of the radicals $R_3$ denoting methyl; the radical $R'_3$ is a $C_2$-$C_{18}$ divalent hydrocarbon-based alkylene chain unit; p ranges from 1 to 30 inclusive; and q ranges from 1 to 150 inclusive;
  acyloxyalkyl groups such as, for example, the polyorganosiloxanes described in U.S. Pat. No. 4,957,732 and corresponding to formula (XII):

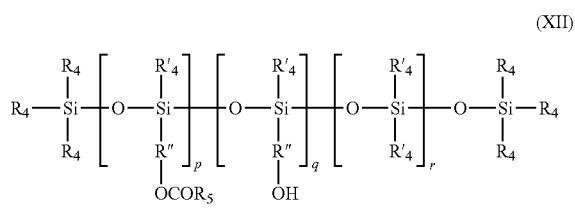
(XII)

wherein:
  $R_4$ is chosen from methyl, phenyl, —$OCOR_5$ and hydroxyl groups, one of the radicals $R_4$ per silicon atom optionally being OH;
  $R'_4$ is chosen from methyl and phenyl groups;
  wherein at least 60 mol % of all the radicals $R_4$ and $R'_4$ are methyl groups;
  $R_5$ is chosen from $C_8$-$C_{20}$ alkyl and alkenyl groups;
  R" is chosen from $C_2$-$C_{18}$ linear and branched divalent hydrocarbon-based alkylene radicals;
  r ranges from 1 to 120 inclusive;
  p ranges from 1 to 30;
  q is equal to 0 or is less than 0.5 p, wherein the sum p+q ranges from 1 to 30;
  the polyorganosiloxanes of formula (XII) may contain groups:

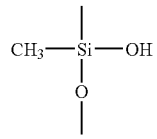

in proportions not exceeding 15% of the sum p+q+r;
  anionic groups of carboxylic type, such as, for example, in the products described in European Patent No. EP 186 507 from the company Chisso Corporation, or of alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names ABIL S201 and ABIL S255;
  hydroxyacylamino groups, such as the polyorganosiloxanes described in European Patent Application No. EP 342 834. Non-limiting mention may be made, for example, of the product Q2-8413 from the company Dow Corning.

According to at least one embodiment of the present disclosure, it is also possible to use silicones comprising a polysiloxane portion and a portion comprising a non-silicone organic chain, one of the two portions constituting the main chain of the polymer, the other being grafted onto the said main chain. These polymers are described, for example, in European Patent Application Nos. EP-A-412 704, EP-A-412 707, EP-A-582 152, and EP-A-640 105; International Patent Application Nos. WO 95/00578 and WO 93/23009; and U.S. Pat. Nos. 4,693,935, 4,728,571 and 4,972,037. In at least one embodiment these polymers are anionic or nonionic.

Such polymers are, for example, copolymers that can be obtained by free-radical polymerization starting with a monomer mixture comprising:
a) 50 to 90% by weight of tert-butyl acrylate;
b) 0 to 40% by weight of acrylic acid;
c) 5 to 40% by weight of silicone macromer of formula:

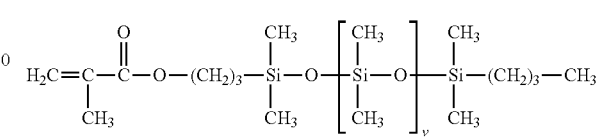
(XIII)

with v being a number ranging from 5 to 700; the weight percentages being calculated relative to the total weight of the monomers.

Other examples of grafted silicone polymers are, for example, polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl (meth) acrylate type.

According to the present disclosure, all of the silicones can also be used in the form of emulsions, nanoemulsions or microemulsions.

The polyorganosiloxanes that are used in accordance with at least one embodiment of the disclosure are:
  non-volatile silicones chosen from the family of polyalkylsiloxanes containing trimethylsilyl end groups, such as oils having a viscosity of between 0.2 and 2.5 m²/s at 25° C., such as the oils of the DC200 series from Dow Corning, including that with a viscosity of 60,000 cSt, the oils of the SILBIONE 70047 and 47 series and the oil 70 047 V 500 000, which are sold by the company Rhodia Chimie, polyalkylsiloxanes containing dimethylsilanol end groups, such as dimethiconols, or polyalkylarylsiloxanes such as the oil SILBIONE 70641 V 200 sold by the company Rhodia Chimie;
  the organopolysiloxane resin sold under the name Dow Corning 593;
  polysiloxanes containing amine groups, such as amodimethicones or trimethylsilylamodimethicones.

In at least one embodiment, the cationic proteins or cationic protein hydrolysates are chemically modified polypeptides bearing quaternary ammonium groups at the end of the chain or grafted thereto. Their molecular mass can range, for example, from 1500 to 10,000 or from 2000 to 5000. Among these compounds, non-limiting mention may be made:
  collagen hydrolysates bearing triethylammonium groups, such as the products sold under the name QUAT-PRO E by the company Maybrook and referred to in the CTFA dictionary as "Triethonium Hydrolyzed Collagen Ethosulfate";
  collagen hydrolysates bearing trimethylammonium and trimethylstearylammonium chloride groups, sold under the name QUAT-PRO S by the company Maybrook and referred to in the CTFA dictionary as "Steartrimonium Hydrolyzed Collagen";
  animal protein hydrolysates bearing trimethylbenzylammonium groups such as the products sold under the name CROTEIN BTA by the company Croda and referred to in the CTFA dictionary as "Benzyltrimonium hydrolyzed animal protein";
  protein hydrolysates bearing, on the polypeptide chain, quaternary ammonium groups containing at least one alkyl radical having from 1 to 18 carbon atoms.

Among these protein hydrolysates, non-limiting mention may be made, inter alia, of:
  CROQUAT L in which the quaternary ammonium groups contain a $C_{12}$ alkyl group;
  CROQUAT M in which the quaternary ammonium groups contain $C_{10}$-$C_{18}$ alkyl groups;
  CROQUAT S in which the quaternary ammonium groups contain a $C_{18}$ alkyl group;
  CROTEIN Q in which the quaternary ammonium groups contain at least one alkyl group having from 1 to 18 carbon atoms.

These various products are sold by the company Croda.

Other quaternized proteins or hydrolysates are, for example, those corresponding to formula (XIV):

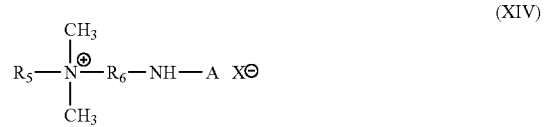

wherein $X^-$ is chosen from anions of organic and mineral acids, A is chosen from protein residues derived from hydrolysates of collagen protein, $R_5$ is chosen from lipophilic groups containing up to 30 carbon atoms and $R_6$ is chosen from alkylene groups having 1 to 6 carbon atoms. Non-limiting mention may be made, for example, of the products sold by the company Inolex under the name LEXEIN QX 3000, referred to in the CTFA dictionary as "Cocotrimonium Collagen Hydrolysate".

Non-limiting mention may also be made of quaternized plant proteins such as wheat, corn or soybean proteins: as quaternized wheat proteins, non-limiting mention may be made of those sold by the company Croda under the names HYDROTRITICUM WQ or QM, referred to in the CTFA dictionary as "Cocodimonium Hydrolysed Wheat Protein", HYDROTRITICUM QL, referred to in the CTFA dictionary as "Lauridimonium Hydrolysed Wheat Protein" or HYDROTRITICUM QS, referred to in the CTFA dictionary as "Steardimonium Hydrolysed Wheat Protein".

According to at least one embodiment of the present disclosure, the compounds of ceramide type are natural or synthetic ceramides and/or glycoceramides and/or pseudoceramides and/or neoceramides.

Compounds of ceramide type are described, for example, in German Patent Application Nos. DE 4 424 530, DE 4 424 533, DE 4 402 929, and DE 4 420 736; International Patent Application Nos. WO 95/23807, WO 94/07844, WO 95/16665, WO 94/07844, WO 94/24097 and WO 94/10131; European Patent Application Nos. EP-A-0 646 572 and EP-A-0 227 994; and French Patent Application No. FR-2 673 179, the teachings of which are included herein by way of reference.

Compounds of ceramide type that are used according to at least one embodiment of the disclosure are, for example:
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and N-stearoylphytosphingosine,
2-N-palmitoylaminohexadecane-1,3-diol,
bis(N-hydroxyethyl-N-cetyl)malonamide,
N-(2-hydroxyethyl)-N-(3-cetyloxy-2-hydroxypropyl)cetylamide,
N-docosanoyl-N-methyl-D-glucamine, or mixtures of these compounds.

According to at least one embodiment of the present disclosure, cationic surfactants are used, among which non-limiting mention may be made of: optionally polyoxyalkylenated primary, secondary or tertiary fatty amine salts; quaternary ammonium salts; imidazoline derivatives; or amine oxides of cationic nature.

Non-limiting examples of quaternary ammonium salts include:

those of formula (XV) below:

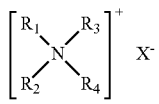

(XV)

wherein the radicals $R_1$ to $R_4$, which may be identical or different, are chosen from linear and branched aliphatic radicals containing from 1 to 30 carbon atoms, and aromatic radicals such as aryl or alkylaryl. The aliphatic radicals can comprise heteroatoms such as, for example, oxygen, nitrogen, sulfur or halogens. The aliphatic radicals are chosen, for example, from alkyl, alkoxy, polyoxy($C_2$-$C_6$)alkylene, alkylamide, ($C_{12}$-$C_{22}$)alkylamido ($C_2$-$C_6$)alkyl, ($C_{12}$-$C_{22}$)alkylacetate and hydroxyalkyl radicals, comprising from about 1 to 30 carbon atoms; $X^-$ is an anion chosen from halides, phosphates, acetates, lactates, ($C_2$-$C_6$)alkyl sulfates and alkyl or alkylaryl sulfonates;

quaternary ammonium salts of imidazolinium, such as, for example, the salt of formula (XVI) below:

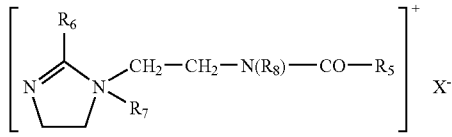

(XVI)

wherein $R_5$ is chosen from alkenyl and alkyl radicals containing from 8 to 30 carbon atoms, for example tallow fatty acid derivatives; $R_6$ is chosen from hydrogen atoms, $C_1$-$C_4$ alkyl radicals and alkenyl or alkyl radicals containing from 8 to 30 carbon atoms; $R_7$ is chosen from $C_1$-$C_4$ alkyl radicals; $R_8$ is chosen from hydrogen atoms and $C_1$-$C_4$ alkyl radicals; $X^-$ is an anion chosen from halides, phosphates, acetates, lactates, alkyl sulfates and alkyl or alkylaryl sulfonates. In at least one embodiment, $R_5$ and $R_6$ denote a mixture of alkenyl or alkyl radicals containing from 12 to 21 carbon atoms, for example tallow fatty acid derivatives, $R_7$ is a methyl radical and $R_8$ is a hydrogen atom. Such a product is sold, for example, under the name "Rewoquat W 75" by the company Degussa;

diquaternary ammonium salts of formula (XVII):

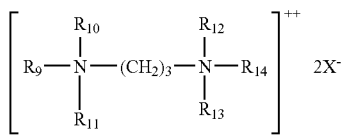

(XVII)

wherein $R_9$ is chosen from aliphatic radicals containing from about 16 to 30 carbon atoms; $R_{10}$, $R_{11}$, $R_{12}$, $R_{13}$ and $R_{14}$, which may be identical or different, are chosen from hydrogen atoms or alkyl radicals containing from 1 to 4 carbon atoms; and $X^-$ is an anion chosen from halides, acetates, phosphates, nitrates and methyl sulfates. Such diquaternary ammonium salts may comprise propane tallow diammonium dichloride; and quaternary ammonium salts containing at least one ester function.

The quaternary ammonium salts containing at least one ester function that may be used according to at least one embodiment of the present disclosure are, for example, those of formula (XVIII) below:

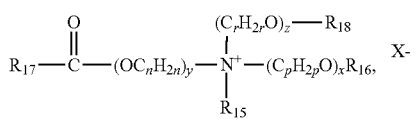

(XVIII)

wherein:

$R_{15}$ is chosen from $C_1$-$C_6$ alkyl radicals and $C_1$-$C_6$ hydroxyalkyl or dihydroxyalkyl radicals;

$R_{16}$ is chosen from:

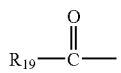

a radical linear and branched, saturated and unsaturated $C_1$-$C_{22}$ hydrocarbon-based radicals $R_{20}$, a hydrogen atom, $R_{18}$ is chosen from:

a radical

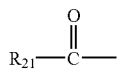

linear and branched, saturated and unsaturated $C_1$-$C_6$ hydrocarbon-based radicals $R_{22}$, a hydrogen atom, $R_{17}$, $R_{19}$ and $R_{21}$, which may be identical or different, are chosen from linear or branched, saturated or unsaturated $C_7$-$C_{21}$ hydrocarbon-based radicals;

n, p and r, which may be identical or different, are integers ranging from 2 to 6;

y is an integer ranging from 1 to 10;

x and z, which may be identical or different, are integers ranging from 0 to 10;

$X^-$ is chosen from simple and complex, organic and inorganic anions; with the proviso that the sum x+y+z is from 1 to 15, that when x is 0, then $R_{16}$ denotes $R_{20}$ and that when z is 0, then $R_{18}$ denotes $R_{22}$.

The $R_{15}$ alkyl radicals may be linear or branched and, in at least one embodiment, linear.

According to at least one embodiment, $R_{15}$ is chosen from methyl, ethyl, hydroxyethyl or dihydroxypropyl radicals, and in at least one further embodiment, methyl and ethyl radicals.

The sum x+y+z ranges from 1 to 10 in at least one embodiment.

When $R_{16}$ is a hydrocarbon-based radical $R_{20}$, it may be long and contain from 12 to 22 carbon atoms, or short and contain from 1 to 3 carbon atoms.

When $R_{18}$ is a hydrocarbon-based radical $R_{22}$, it may contain 1 to 3 carbon atoms.

In at least one embodiment, $R_{17}$, $R_{19}$ and $R_{21}$, which may be identical or different, are chosen from linear and branched, saturated and unsaturated $C_{11}$-$C_{21}$ hydrocarbon-based radicals, such as, for example, from linear and branched, saturated and unsaturated, $C_{11}$-$C_{21}$ alkyl and alkenyl radicals.

According to at least one embodiment, x and z, which may be identical or different, are 0 or 1.

In at least one embodiment, y is equal to 1.

In at least one embodiment, n, p and r, which may be identical or different, are 2 or 3, such as, for example, equal to 2.

The anion, in at least one embodiment, is chosen from halides (chloride, bromide or iodide) and alkyl sulfates, such as methyl sulfate. However, methanesulfonate, phosphate, nitrate, tosylate, an anion derived from an organic acid, such as acetate or lactate, or any other anion that is compatible with the ammonium containing an ester function, may also be used.

The anion $X^-$ is chloride or methyl sulfate in at least one embodiment.

The ammonium salts used according to at least one embodiment, are those of formula (XVIII) in which:
  $R_{15}$ is chosen from methyl and ethyl radicals,
  x and y are equal to 1;
  z is equal to 0 or 1;
  n, p and r are equal to 2;
  $R_{16}$ is chosen from:
    a radical

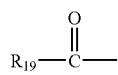

methyl, ethyl or $C_4$-$C_{22}$ hydrocarbon-based radicals;
  a hydrogen atom;
  $R_{18}$ is chosen from:
    a radical

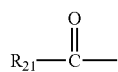

a hydrogen atom;
  $R_{17}$, $R_{19}$ and $R_{21}$, which may be identical or different, are chosen from linear and branched, saturated and unsaturated $C_{13}$-$C_{17}$ hydrocarbon-based radicals, such as, for example, from linear and branched, saturated and unsaturated $C_{13}$-$C_{17}$ alkyl and alkenyl radicals.

The hydrocarbon-based radicals are linear in at least one embodiment.

Non-limiting examples that may be mentioned include the compounds of formula (XVI) such as the diacyloxyethyldimethylammonium, diacyloxyethylhydroxyethylmethylammonium, mono-acyloxyethyidihydroxyethylmethylammonium, triacyloxyethylmethylammonium and monoacyloxyethylhydroxyethyldimethylammonium salts (such as chloride or methyl sulfate), and mixtures thereof. In at least one embodiment, the acyl radicals contain 14 to 18 carbon atoms and are obtained from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (such as a methyl or ethyl halide), a dialkyl sulfate (such as dimethyl or diethyl sulfate), methyl methanesulfonate, methyl para-toluenesulfonate, glycol chlorohydrin or glycerol chlorohydrin.

Such compounds are sold, for example, under the names DEHYQUART by the company Cognis, STEPANQUAT by the company Stepan, NOXAMIUM by the company CECA or REWOQUAT WE 18 by the company Degussa.

It is also possible to use the ammonium salts containing at least one ester function that are described in U.S. Pat. Nos. 4,874,554 and 4,137,180.

Among the quaternary ammonium salts of formula (XV) used according to at least one embodiment, non-limiting mention may be made of tetraalkylammonium chlorides such as, for example, dialkyldimethylammonium chlorides or alkyltrimethylammonium chlorides, in which the alkyl radical contains from about 12 to 22 carbon atoms, including behenyltrimethylammonium chloride, distearyidimethylammonium chloride, cetyltrimethyl-ammonium chloride, or benzyldimethylstearylammonium chloride, or, on the other hand, stearamidopropyldimethyl(myristyl acetate)ammonium chloride sold under the name CERAPHYL 70 by the company Van Dyk.

The fatty acids may be chosen from, for example, myristic acid, palmitic acid, stearic acid, behenic acid, oleic acid, linoleic acid, linolenic acid and isostearic acid.

In at least one embodiment, the fatty acid derivatives are carboxylic acid esters, such as mono-, di-, tri- or tetracarboxylic esters.

The monocarboxylic acid esters are, for example, linear or branched, saturated or unsaturated $C_1$-$C_{26}$ aliphatic acid monoesters of linear or branched, saturated or unsaturated, $C_1$-$C_{26}$ aliphatic alcohols, the total carbon number of these esters being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isostearyl neopentanoate, and isodecyl neopentanoate.

$C_4$-$C_{22}$ di- or tricarboxylic acid esters of $C_1$-$C_{22}$ alcohols and mono-, di- or tricarboxylic acid esters of $C_2$-$C_{26}$ di-, tri-, tetra- or pentahydroxy alcohols can also be used.

Non-limiting mention may be made of: diethyl sebacate; diisopropyl sebacate; diisopropyl adipate; di-n-propyl adipate; dioctyl adipate; diisostearyl adipate; dioctyl maleate; glyceryl undecylenate; octyldodecylstearoyl stearate; pentaerythrityl monoricinoleate; penta-erythrityl tetraisononanoate; pentaerythrityl tetrapelargonate; pentaerythrityl tetraisostearate; pentaerythrityl tetraoctanoate; propylene glycol dicaprylate dicaprate; tridecyl erucate; triisopropyl citrate; triisostearyl citrate; glyceryl trilactate; glyceryl trioctanoate; trioctyldodecyl citrate; trioleyl citrate.

Among the esters mentioned above, at least one embodiment can use ethyl and isopropyl palmitates, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate, cetyl octanoate, isostearyl neopentanoate, isodecyl neopentanoate.

The fluoro oils are, for example, the perfluoropolyethers described, for example, in European Patent Application No. EP-A-486 135 and the fluorohydrocarbon compounds described, for example, in International Patent Application No. WO 93/11103. The teaching of these two patent applications is included in its entirety in the present disclosure by way of reference.

The term "fluorohydrocarbon compounds" denotes compounds whose chemical structure contains a carbon skeleton in which certain hydrogen atoms have been replaced with fluorine atoms.

The fluoro oils can also be fluorocarbons such as fluoroamines, for example perfluorotributylamine, fluorohydrocarbons, for example perfluorodecahydronaphthalene, fluoro esters and fluoro ethers.

The perfluoropolyethers are sold, for example, under the trade names FOMBLIN by the company Montefluos and KRYTOX by the company Du Pont.

Among the fluorohydrocarbon compounds that may be used according to the present disclosure, non-limiting mention may also be made of fluorine-containing fatty acid esters such as the product sold under the name NOFABLE FO by the company Nippon Oil.

Needless to say, it is possible to use mixtures of conditioning agents.

According to the present disclosure, the conditioning agent(s) may be present in an amount ranging from 0.001% to 20% by weight, such as, for example, from 0.01% to 10% by weight or from 0.1% to 3% by weight, relative to the total weight of the final composition.

The compositions according to the present disclosure may be in the form of aqueous or aqueous-alcoholic haircare lotions. The cosmetic compositions according to the present disclosure may also be in the form of a gel, a milk, a cream, an emulsion or a mousse, and may be used on the hair.

The compositions may be packaged in various forms, such as vaporizers, pump-dispenser bottles or in aerosol containers in order to apply the composition in vaporized form or in the form of a mousse. Such packaging forms are indicated, for example, when it is desired to obtain a spray, a lacquer or a mousse for treating the hair.

The pH of the composition applied to the keratin fibers may range from 1 to 11. In at least one embodiment, the pH ranges from 2 to 6, and may be adjusted to the desired value by means of acidifying or basifying agents that are well known in the prior art for compositions applied to keratin fibers.

Among the basifying agents that may be used according to the present disclosure, non-limiting mention may be made, for example, of aqueous ammonia, alkali metal carbonates, alkanolamines such as monoethanolamine, diethanolamine and triethanolamine and also derivatives thereof, oxyethylenated and/or oxypropylenated hydroxyalkylamines and ethylenediamines, sodium hydroxide, potassium hydroxide and the compounds having the following formula:

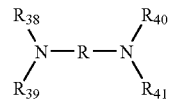

wherein R is a propylene residue optionally substituted with a hydroxyl group or a $C_1$-$C_4$ alkyl radical; $R_{38}$, $R_{39}$, $R_{40}$ and $R_{41}$, which may be identical or different, are chosen from hydrogen atoms, $C_1$-$C_4$ alkyl radicals and $C_1$-$C_4$ hydroxyalkyl radicals.

The acidifying agents are conventionally, for example, mineral or organic acids, for instance hydrochloric acid, orthophosphoric acid, carboxylic acids, for instance tartaric acid, citric acid or lactic acid, or sulfonic acids.

According to at least one embodiment, the treatment process is applied to keratin fibers, such as hair dyed by direct dyeing or oxidation dyeing.

Another aspect of the present disclosure relates to the use of the process for protecting keratin fibers against the action of atmospheric agents, such as against the action of light.

One aspect of the present disclosure relates to the use of the said process as a post-treatment to oxidation dyeing or direct dyeing of keratin fibers, such as the hair.

Another aspect of the present disclosure relates to a process for dyeing keratin fibers, such as human hair, comprising:
a) direct dyeing or oxidation dyeing the fibers,
b) applying to the fibers a composition comprising, in a physiologically acceptable and cosmetically acceptable medium, at least one protective agent with a log P of less than or equal to 6,
c) applying to the fibers a liquid water/steam mixture at a temperature of at least 35° C.

At least one process mode for dyeing fibers according to the present disclosure comprises:
1) applying to the fibers a direct or oxidation dye composition (A) for a time that is sufficient to develop the color,
2) optionally, rinsing and/or washing the fibers with shampoo and/or partially or totally drying the fibers,
3) applying a composition (B) comprising at least one protective agent as defined above not containing any oxidation dye or any oxidizing agent to the fibers,
4) optionally, rinsing and/or washing the fibers with shampoo and/or partially or totally drying the fibers,
5) applying a liquid water/steam mixture at a temperature of at least 35° C. to the fibers,
6) optionally, rinsing and/or washing the fibers with shampoo and/or partially or totally drying the fibers.

According to at least one embodiment of the present disclosure, the process mode for dyeing fibers comprises:
1) applying to the fibers a composition (B) comprising at least one protective agent as defined above not containing any oxidation dye or any oxidizing agent,
2) optionally, rinsing and/or washing the fibers with shampoo and/or partially or totally drying the fibers,
3) applying a liquid water/steam mixture at a temperature of at least 35° C. to the fibers,
4) applying a direct or oxidation dye composition (A) to the fibers for a time that is sufficient to develop the color, and
5) optionally, rinsing and/or washing the fibers with shampoo and/or partially or totally drying the fibers.

In the various dyeing process modes according to the present disclosure, the composition (B) comprising the at least one protective agent may be applied immediately after dyeing, or after a delay. The term "after a delay" refers to an application made a few hours, one day or several days (from 1 to 60 days) after the dyeing operation. In at least one embodiment, composition (B) is applied immediately after dyeing the keratin fibers.

The nature and concentration of the dyes present in the dye composition (A) is not critical.

In the case of lightening direct dyeing operations, the dye compositions (A) may result from the mixing, at the time of use, of a dye composition (A1) containing at least one direct dye and a composition (A2) containing an oxidizing agent.

In the case of oxidation dyeing, the dye compositions (A) may result from the mixing, at the time of use, of a dye composition (A1) containing at least one oxidation base and optionally at least one coupler and/or a direct dye and of a composition (A2) containing an antioxidant.

In at least one embodiment, the direct dyes are compounds that absorb light radiation in the visible range (400-750 nm). They may be of nonionic, anionic or cationic nature.

According to at least one embodiment, the direct dyes are chosen from nitrobenzene dyes and azo, anthraquinone, naphthoquinone, benzoquinone, phenothiazine, indigoid, xanthene, phenanthridine, phthalocyanine and triarylmethane-based dyes, alone or as mixtures.

Among the nitrobenzene dyes that may be used according to the present disclosure, non-limiting mention may be made of the following red or orange compounds: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-aminodiphenylamine, 1-amino-3-nitro-6-hydroxybenzene, 1-(β-aminoethyl)amino-2-nitro-4-(β-hydroxyethyloxy)benzene, 1-(β,γ-dihydroxypropyl)oxy-3-nitro-4-(β-hydroxyethyl)aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine, 1-amino-2-nitro-4-hydroxy-5-methylbenzene, alone or as mixtures.

Among nitrobenzene direct dyes that may be used according to the present disclosure, non-limiting mention may be made of dyes of yellow and green-yellow type, for instance 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-aminoethyl)amino-2-nitro-5-methoxybenzene, 1,3-bis(β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureidoethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Blue or violet nitrobenzene dyes that may be used in at least one embodiment include, for instance, 1-(β-hydroxyethyl)amino-4-N,N-bis(β-hydroxyethyl)amino-2-nitrobenzene, 1-(γ-hydroxypropyl)amino-4-N, N-bis(β-hydroxyethyl)amino-2-nitrobenzene, 1-(β-hydroxyethyl)amino-4-(N-methyl, N-β-hydroxyethyl)amino-2-nitrobenzene, 1-(β-hydroxyethyl)amino-4-(N-ethyl, N-β-hydroxyethyl)amino-2-nitrobenzene, 1-(β,γ-dihydroxypropyl)amino-4-(N-ethyl, N-β-hydroxyethyl)amino-2-nitrobenzene, the 2-nitro-para-phenylenediamines of the following formula:

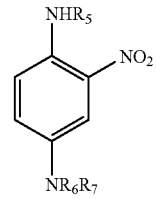

wherein:
R$_6$ is chosen from C$_1$-C$_4$ alkyl radicals and β-hydroxyethyl, β-hydroxypropyl or γ-hydroxypropyl radicals;
R$_5$ and R$_7$, which may be identical or different, are chosen from β-hydroxyethyl, β-hydroxypropyl, γ-hydroxypropyl or β,γ-dihydroxypropyl radicals, at least one of the radicals R$_6$, R$_7$ or R$_5$ is chosen from γ-hydroxypropyl radicals and R$_6$ and R$_7$ do not simultaneously denote a β-hydroxyethyl radical when R$_6$ is a γ-hydroxypropyl radical, such as those described in French Patent No. FR 2 692 572.

It is recalled that azo dyes are compounds comprising in their structure at least one —N=N— sequence not included in a ring; methine dyes are compounds comprising in their structure at least one —C=C— sequence not included in a ring; azomethine dyes are compounds comprising in their structure at least one —C=N— sequence not included in a ring.

The triarylmethane-based dyes comprise in their structure at least one sequence below:

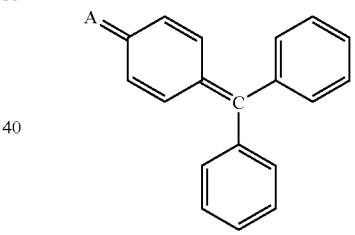

A is an oxygen or nitrogen atom.

The xanthene dyes comprise in their structure at least one sequence of formula:

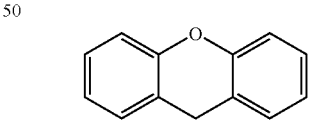

The phenanthridine dyes comprise in their structure at least one sequence of formula:

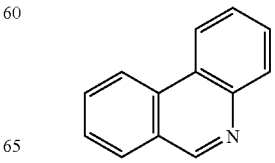

The phthalocyanine dyes comprise in their structure at least one sequence of formula:

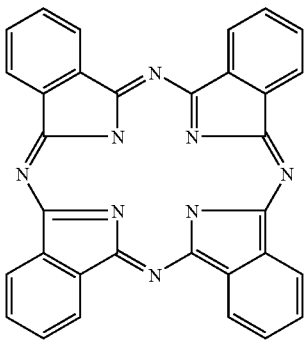

The phenothiazine dyes comprise in their structure at least one sequence below:

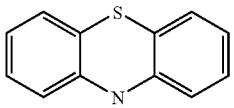

The direct dyes may moreover be chosen from basic dyes like those listed in the Color Index, 3rd edition, under the names "Basic Brown 16", "Basic Brown 17", "Basic Yellow 57", "Basic Red 76", "Basic Violet 10", "Basic Blue 26" and "Basic Blue 99"; or from the acidic direct dyes listed in the Color Index, 3rd edition, under the names "Acid Orange 7", "Acid Orange 24", "Acid Yellow 36", "Acid Red 33", "Acid Red 184", "Acid Black 2", "Acid Violet 43", and "Acid Blue 62", or cationic direct dyes such as those described in International Patent Application Nos. WO 95/01772 and WO 95/15144, and European Patent Application No. EP 714 954, and "Basic Red 51", "Basic Orange 31" and "Basic Yellow 87", the content of which forms an integral part of the present disclosure.

When they are present, the at least one direct dye may be present in an amount ranging from 0.0005% to 12% by weight relative to the total weight of the dye composition, such as, for example, from 0.005% to 6% by weight relative to the total weight of the dye composition.

The oxidation bases may be chosen from the oxidation bases conventionally used in oxidation dyeing and among which non-limiting mention may be made of para-phenylenediamines, bis(phenyl)alkylenediamines, para-aminophenols, ortho-aminophenols and heterocyclic bases.

Among the para-phenylenediamines that may be used according to at least one embodiment, non-limiting mention may be made of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, N,N-diethyl-4-amino-3-methylaniline, N,N-bis(β-hydroxyethyl)-para-phenylenediamine, 4N,N-bis(β-hydroxyethyl)-amino-2-methylaniline, 4N,N-bis(β-hydroxyethyl)amino-2-chloro-paraaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxy-ethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine and N-(β-methoxyethyl)-para-phenylenediamine, and the acid-addition salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid-addition salts thereof, are used in at least one embodiment.

Among the bis(phenyl)alkylenediamines that may be used according to at least one embodiment, non-limiting mention may be made of, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methyl-aminophenyl)tetramethylenediamine, N,N'-bis(ethyl)-N,N'-bis(4'-amino-3'-methylphenyl)-ethylenediamine and 1,8-bis(2,5-diaminophenoxy)-3,5-dioxaoctane, and the acid-addition salts thereof.

Among the para-aminophenols that may be used according to at least one embodiment, non-limiting mention may be made of, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethyl-phenol, 4-amino-2-aminomethylphenol, 4-amino-2-(β-hydroxyethylaminomethyl)phenol and 4-amino-2-fluorophenol, and the acid-addition salts thereof.

Among the ortho-aminophenols that may be used according to at least one embodiment, non-limiting mention may be made of, for example, 2-aminophenol, 2-amino-5-methylphenol, 2-amino-6-methylphenol and 5-acetamido-2-aminophenol, and the acid-addition salts thereof.

Among the heterocyclic bases that may be used according to at least one embodiment, non-limiting mention may be made of, for example, pyridine derivatives, pyrimidine derivatives and pyrazole derivatives.

Among the pyridine derivatives that may be used according to at least one embodiment, non-limiting mention may be made of the compounds described, for example, in British Patent Nos. GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Among the pyrimidine derivatives that may be used according to at least one embodiment, non-limiting mention may be made of the compounds described, for example, in German Patent No. DE 2 359 399; Japanese Patent Nos. JP 88-169571 and JP 05-163124; European Patent No. EP 0 770 375 or International Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triamino-pyrimidine, and pyrazolopyrimidine derivatives such as those mentioned in French Patent Application No. FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-amino-pyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl) (2-hydroxyethyl)amino]ethanol, 2-[(7-aminopyrazolo[1,5-a]pyrimidin-3-yl) (2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid-addition salts thereof and the tautomeric forms thereof, when a tautomeric equilibrium exists.

Among the pyrazole derivatives that may be used according to at least one embodiment, non-limiting mention may be made of the compounds described in German Patent Nos. DE 3 843 892 and DE 4 133 957; International Patent Application Nos. WO 94/08969 and WO 94/08970; French Patent Application No. FR-A-2 733 749; and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydra-zinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the acid-addition salts thereof.

When they are used, these oxidation bases may be present in an amount ranging from 0.0005% to 12% by weight relative to the total weight of the dye composition, such as from 0.005% to 6% by weight relative to this weight.

The oxidation dye compositions in accordance with at least one embodiment of the present disclosure may also contain at least one coupler and/or at least one direct dye, for example, to modify the shades or to enrich them with tints.

The couplers that may be used in the oxidation dye compositions in accordance with at least one embodiment of the present disclosure may be chosen from the couplers conventionally used in oxidation dyeing, and among which non-limiting mention may be made of meta-phenylenediamines, meta-aminophenols, meta-diphenols, naphthols and heterocyclic couplers, for instance indole derivatives, indoline derivatives, pyridine derivatives, indazole derivatives, pyrazolo[1,5-b]-1,2,4-triazole derivatives, pyrazolo[3,2-c]-1,2,4-triazole derivatives, benzimidazole derivatives, benzothiazole derivatives, benzoxazole derivatives, 1,3-benzodioxole derivatives and pyrazolones, and the acid-addition salts thereof.

These couplers may also be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 6-hydroxybenzomorpholine, 3,5-diamino-2,6-dimethoxy-pyridine, 1-N(β-hydroxyethyl)amino-3,4-methylenedioxy-benzene, 2,6-bis(β-hydroxyethyleneamino)toluene, 2,6-dihydroxy-4-methylpyridine, 1H-3-methylpyrazol-5-one, 1-phenyl-3-methylpyrazol-5-one, and the acid-addition salts thereof.

When they are present, the at least one coupler may be present in an amount ranging from 0.0001% to 10% by weight relative to the total weight of the dye composition, such as, for example, from 0.005% to 5% by weight relative to this weight.

The dye composition in accordance with at least one embodiment of the present disclosure may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetrants, sequestrants, fragrances, buffers, dispersants, conditioning agents, for instance silicones, film-forming agents, preserving agents and opacifiers.

Needless to say, a person skilled in the art will take care to select this or these optional additional compound(s) such that the advantageous properties intrinsically associated with the oxidation dye composition in accordance with the present disclosure are not, or are not substantially, adversely affected by the envisaged addition(s).

The dye composition according to the present disclosure may be in various forms, such as in the form of liquids, creams or gels, or in any other form that is suitable for dyeing keratin fibers, such as human hair.

The nature of the oxidizing agent used in the lightening direct dyeing operation (direct dyeing with an oxidizing agent) or in the oxidation dyeing operation is not critical.

In at least one embodiment, the oxidizing agent is chosen from hydrogen peroxide, urea peroxide, alkali metal bromates or ferricyanides, and persalts such as perborates and persulfates. At least one redox enzyme such as laccases, peroxidases and two-electron oxidoreductases (such as uricase) may also be used, where appropriate in the presence of the respective donor or cofactor thereof.

According to at least one embodiment of the present disclosure, the process of the disclosure may be used on hair that has been sensitized by hair treatments other than those of the disclosure that are mentioned above.

The invention will now be illustrated more fully with the aid of the examples that follow, which should not be considered as limiting it to the described embodiments. Throughout the text hereinbelow or hereinabove, the percentages are expressed on a weight basis. In the examples, AM means active material.

Other than in the operating examples, or where otherwise indicated, all numbers expressing quantities of ingredients, reaction conditions, and so forth iused in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the invention as approximations, the numerical values set forth in the specific examples are reported as precisely as possible. Any numerical value, however, inherently contains certain errors necessarily resulting from the standard deviation found in its respective testing measurement.

The examples that follow are intended to illustrate the invention without, however, being limiting in nature.

EXAMPLES

Example 1

Dyeing Step

At the time of use, the composition 1 defined below was mixed weight-for-weight with aqueous hydrogen peroxide solution (L'Oréal professional 20-volumes aqueous hydrogen peroxide solution, at 6%).

The mixture was then applied to locks of permanent-waved hair containing 90% white hairs, at a rate of 10 g of dye mixture/g of lock. The leave-on time was 15 minutes on each side of the lock. The dyeing was then stopped by rinsing with water.

| Dye composition 1 | Amounts in grams |
| --- | --- |
| Oleyl alcohol polyglycerolated with 2 mol of glycerol | 4 |
| Oleyl alcohol polyglycerolated with 4 mol of glycerol (78% AM) | 5.69 |
| Oleic acid | 3 |
| Oleylamine 2 EO sold under the name ETHOMEEN O12 by the company Akzo | 7 |
| Dimethaminopropyl laurylaminosuccinamate, sodium salt, at 55% AM | 3 |
| Oleyl alcohol | 5 |
| Oleic acid diethanolamide | 12 |
| Propylene glycol | 3.5 |
| Ethyl alcohol | 7 |
| Dipropylene glycol | 0.5 |
| Propylene glycol monomethyl ether | 9 |
| p-Phenylenediamine | $6 \times 10^{-4}$ mol |
| 2,4-diaminophenoxyethanol HCl | $6 \times 10^{-4}$ mol |
| Sodium metabisulfite as an aqueous solution containing 35% AM | 0.455 |
| Ammonium acetate | 0.8 |
| Antioxidant, sequestrant | qs |
| Fragrance, preserving agent | qs |
| Aqueous ammonia containing 20% $NH_3$ | 10 |
| Demineralized water | qs 100 |

Protective Treatment Steps

A protective treatment was performed on the dyed locks by applying composition 2 indicated below, at a rate of 2 g/g of hair. A liquid water/steam mixture maintained at 45° C. by the Micromist apparatus sold by the company Takara Belmont was then applied for 10 minutes.

| Composition 2 | Amounts in grams |
| --- | --- |
| Benzyl alcohol | 4.0 g |
| Benzoic acid | 0.2 g |
| Benzophenone-4 | 5.0 g |
| Citric acid/trisodium citrate/triethanolamine buffer | qs pH = 4 |

-continued

| Composition 2 | Amounts in grams |
| --- | --- |
| Hydroxyethylcellulose | 1.2 g |
| Xanthan gum | 0.4 g |
| Preserving agents | qs |
| Water | qs 100 g |

The locks were then washed with DOP camomile shampoo and dried.

A panel of 10 individuals evaluated the effects of the treatment on dyed hair compared with dyed hair that had not undergone treatment:
  1) color fastness after washing with shampoo,
  2) color fastness after exposure to UV/visible light,
  3) color fastness after washing with shampoo and exposure to light.

Color Fastness Steps After Shampooing:

Some of the treated locks were subjected to a test of washing 6 times successively with DOP camomile shampoo, compared with untreated dyed locks.

Color Fastness Steps After UV/visible Light Exposure:

Another portion of the treated locks underwent exposure to UV/visible light, compared with untreated dyed locks.

To do this, the locks were exposed to UV over half their length for a period of 18 hours with a xenon lamp sun simulator that reproduced a reproducible light spectrum similar to that of sunlight (Suntest XLS sold by the company Atlas). The other half of the lock was masked with cardboard.

Color Fastness Steps After Shampooing and then Exposing to UV/visible Light

Another portion of the treated locks was subjected to a test of washing 6 times successively with DOP camomile shampoo and then exposed to UV/visible light under the conditions described previously, compared with untreated dyed locks.

Results:

The 10 individuals of the panel unanimously indicated that the dyed locks which had undergone the protective treatment of the disclosure showed, relative to the untreated dyed locks:
  (1) better resistance of the original color with respect to shampooing,
  (2) better resistance of the original color with respect to light,
  (3) better color fastness after washing with shampoo and exposure to light.

What is claimed is:

1. A process for treating keratin fibers artificially dyed by direct dyeing or by oxidation dyeing, comprising:
  applying to the keratin fibers a composition not containing any oxidation dye or any oxidizing agent and comprising, in a physiologically acceptable medium, at least one protective agent chosen from water-soluble and liposoluble organic UV-screening agents with a log P of less than or equal to 6, and
  then, applying to the keratin fibers a liquid water/steam mixture at a temperature ranging from 35° C. to 45° C.,
  wherein said organic UV-screening agents are chosen from cinnamic derivatives and benzophenone derivatives.

2. The process according to claim 1, wherein said keratin fibers are human hair.

3. The process according to claim 1, wherein the liquid water/steam mixture further comprises at least one other gas or vaporizable compound.

4. The process according to claim 1, wherein the liquid water/steam mixture is placed in contact with the keratin fibers for a time ranging from 1 second to 1 hour.

5. The process according to claim 4, wherein the liquid water/steam mixture is placed in contact with the keratin fibers for a time ranging from 5 minutes to 15 minutes.

6. The process according to claim 1, further comprising cooling the keratin fibers treated with the liquid water/steam mixture by sending over or through them a stream of cold air or a stream of air at ambient temperature.

7. The process according to claim 1, wherein the liposoluble organic UV-screening agents are chosen from:
Ethylhexyl methoxycinnamate, and Benzophenone-3.

8. The process according to claim 1, wherein the at least one protective agent has a log P of less than 4.5.

9. The process according to claim 8, wherein the at least one protective agent has a log P of less than 2.

10. The process according to claim 1, wherein the at least one protective agent is soluble to at least 0.5% in water or $C_1$-$C_4$ lower alcohols at 25° C.

11. The process according to claim 1, wherein the at least one protective agent has in its structure at least one acid function in free or partially or totally salified form.

12. The process according to claim 11, wherein the at least one protective agent has in its structure at least one sulfonic acid function in free or partially or totally salified form.

13. The process according to claim 1, wherein the at least one protective agent is chosen from water-soluble organic UV-screening agents.

14. The process according to claim 13, wherein the at least one water-soluble organic UV-screening agent is chosen from:
Benzophenone-4
Benzophenone-5, and
Benzophenone-9, and mixtures thereof.

15. The process according to claim 14, wherein the at least one water-soluble organic UV-screening agent is Benzophenone-4.

16. The process according to claim 1, wherein the at least one protective agent is present in an amount ranging from 0.15% to 50% by weight relative to the total weight of the composition.

17. The process according to claim 16, wherein the at least one protective agent is present in an amount ranging from 0.5% to 20% by weight relative to the total weight of the composition.

18. The process according to claim 1, wherein the physiologically acceptable medium comprises water or a mixture of water and at least one cosmetically acceptable organic solvent.

19. The process according to claim 18, wherein the at least one cosmetically acceptable organic solvent is chosen from $C_1$-$C_4$ lower alkanols; polyols and polyol ethers; and mixtures thereof.

20. The process according to claim 1, wherein the composition further comprises at least one additive chosen from anionic, cationic, nonionic, amphoteric and zwitterionic surfactants or mixtures thereof; anionic, cationic, nonionic, amphoteric or zwitterionic polymers or mixtures thereof; mineral or organic thickeners; penetrants; sequestrants; fragrances; buffers; dispersants; conditioning agents; film-forming agents; ceramides; preserving agents; and opacifiers.

21. The process according to claim 20, wherein the at least one mineral or organic thickener is chosen from anionic, cationic, nonionic, and amphoteric polymeric associative thickeners.

22. The process according to claim 20, wherein the at least one conditioning agents are chosen from volatile and non-volatile, modified and unmodified silicones.

23. The process according to claim 1, wherein the composition further comprises at least one aromatic alcohol and at least one aromatic carboxylic acid or salt thereof.

24. The process according to claim 23, wherein the at least one aromatic alcohol is present in an amount ranging from 0.01% to 50% by weight relative to the total weight of the composition.

25. The process according to claim 24, wherein the at least one aromatic alcohol is present in an amount ranging from 1% to 20% by weight relative to the total weight of the composition.

26. The process according to claim 23, wherein the at least aromatic alcohol is present in an amount greater than 1% by weight relative to the total weight of the composition.

27. The process according to claim 23, wherein the at least one aromatic alcohol is benzyl alcohol.

28. The process according to claim 23, wherein the at least one aromatic carboxylic acid or salt thereof is present in an amount ranging from 0.001% to 30% by weight relative to the total weight of the composition.

29. The process according to claim 28, wherein the at least one aromatic carboxylic acid or salt thereof is present in an amount ranging from 0.1% to 10% by weight relative to the total weight of the composition.

30. The process according to claim 23, wherein the at least one aromatic carboxylic acid is benzoic acid.

31. The process according to claim 1, wherein the composition further comprises at least one conditioning agent.

32. The process according to claim 31, wherein the at least one conditioning agent is present in an amount ranging from 0.001% to 20% by weight relative to the total weight of the final composition.

33. The process according to claim 32, wherein the at least one conditioning agent is present in an amount ranging from 0.1% to 3% by weight relative to the total weight of the final composition.

34. The process according to claim 1, wherein the composition is in a form chosen from an aqueous or aqueous-alcoholic lotion; a gel; a milk; a cream; an emulsion; and a mousse.

35. The process according to claim 1, wherein the composition is packaged in a form chosen from a vaporiser, a pump-dispenser bottle and an aerosol container.

36. The process according to claim 1, wherein the pH of the composition applied to the keratin fibers ranges from 1 to 11.

37. The process according to claim 36, wherein the pH of the composition ranges from 2 to 6.

38. A process for protecting keratin fibers against the action of atmospheric agents comprising:
applying to the keratin fibers a composition not containing any oxidation dye or any oxidizing agent and comprising, in a physiologically acceptable medium, at least one protective agent chosen from water-soluble and liposoluble organic UV-screening agents with a log P of less than or equal to 6, and
then, applying to the keratin fibers a liquid water/steam mixture at a temperature ranging from 35° C. to 45° C., wherein said organic UV-screening agents are chosen from cinnamic derivatives and benzophenone derivatives.

39. The process according to claim 38, wherein said atmospheric agent is light.

40. A process for dyeing keratin fibers, comprising:
a) direct dyeing or oxidation dyeing the keratin fibers,
b) applying a composition not containing any oxidation dye or any oxidizing agent and comprising, in a physiologically acceptable medium, at least one protective agent chosen from water-soluble and liposoluble organic UV-screening agents with a log P of less than or equal to 6 to the keratin fibers, wherein said organic UV-screening agents are chosen from cinnamic derivatives and benzophenone derivatives, and c) applying a liquid water/steam mixture at a temperature ranging from 35° C. to 45° C. to the keratin fibers.

41. A process for dyeing keratin fibers, comprising:
1) applying a direct or oxidation dye composition (A) to the keratin fibers for a time that is sufficient to develop the color,
2) optionally, rinsing and/or washing the keratin fibers with shampoo and/or partially or totally drying the keratin fibers,
3) applying a composition (B) not containing any oxidation dye or any oxidizing agent and comprising, in a physiologically acceptable medium, at least one protective agent chosen from water-soluble and liposoluble organic UV-screening agents with a log P of less than or equal to 6, to the keratin fibers, wherein said organic UV-screening agents are chosen from cinnamic derivatives and benzophenone derivatives,
4) optionally, rinsing and/or washing the keratin fibers with shampoo and/or partially or totally drying the keratin fibers,
5) applying to the keratin fibers a liquid water/steam mixture at a temperature ranging from 35° C. to 45° C.,
6) optionally, rinsing and/or washing the keratin fibers with shampoo and/or partially or totally drying the keratin fibers.

42. A process for dyeing keratin fibers, comprising:
1) applying a composition (B) not containing any oxidation dye or any oxidizing agent and comprising, in a physiologically acceptable medium, at least one protective agent chosen from water-soluble and liposoluble organic UV-screening agents with a log P of less than or equal to 6, to the keratin fibers, wherein said organic UV-screening agents are chosen from cinnamic derivatives and benzophenone derivatives,
2) optionally, rinsing and/or washing the keratin fibers with shampoo and/or partially or totally drying the keratin fibers,
3) applying to the keratin fibers a liquid water/steam mixture at a temperature ranging from 35° C. to 45° C.,
4) applying a direct or oxidation dye composition (A) to the keratin fibers for a time that is sufficient to develop the color,
5) optionally, rinsing and/or washing the keratin fibers with shampoo and/or partially or totally drying the keratin fibers.

\* \* \* \* \*

UNITED STATES PATENT AND TRADEMARK OFFICE
CERTIFICATE OF CORRECTION

| | | |
|---|---|---|
| PATENT NO. | : 7,998,464 B2 | Page 1 of 1 |
| APPLICATION NO. | : 11/528454 | |
| DATED | : August 16, 2011 | |
| INVENTOR(S) | : Boris Lalleman | |

It is certified that error appears in the above-identified patent and that said Letters Patent is hereby corrected as shown below:

IN THE CLAIMS:

In column 35, line 66, claim 22: "one conditioning agents are chosen" should read
--one conditioning agent is chosen--.

In column 36, lines 12-13, claim 26: "at least aromatic alcohol" should read
--at least one aromatic alcohol--.

In column 36, line 42, claim 35: "vaporiser," should read --vaporizer,--.

Signed and Sealed this
First Day of November, 2011

David J. Kappos
*Director of the United States Patent and Trademark Office*